(12) United States Patent
Chen et al.

(10) Patent No.: US 11,051,760 B2
(45) Date of Patent: Jul. 6, 2021

(54) WEARABLE DEVICE FOR HEALTHCARE AND METHOD THEREOF

(71) Applicant: Belun Technology Company Limited, Hong Kong (HK)

(72) Inventors: Hung Tat Chen, Hong Kong (HK); Kwan Wai To, Hong Kong (HK); Wenbo Gu, Hong Kong (HK)

(73) Assignee: Belun Technology Company Limited, Hong Kong (HK)

( * ) Notice: Subject to any disclaimer, the term of this patent is extended or adjusted under 35 U.S.C. 154(b) by 424 days.

(21) Appl. No.: 15/551,283

(22) PCT Filed: May 9, 2017

(86) PCT No.: PCT/CN2017/083636
§ 371 (c)(1),
(2) Date: Aug. 16, 2017

(87) PCT Pub. No.: WO2017/193915
PCT Pub. Date: Nov. 16, 2017

(65) Prior Publication Data
US 2018/0132789 A1 May 17, 2018

Related U.S. Application Data

(60) Provisional application No. 62/365,978, filed on Jul. 22, 2016, provisional application No. 62/333,785, filed on May 9, 2016.

(51) Int. Cl.
*A61B 5/1455* (2006.01)
*A61B 5/00* (2006.01)
(Continued)

(52) U.S. Cl.
CPC .......... *A61B 5/6826* (2013.01); *A61B 5/0205* (2013.01); *A61B 5/02416* (2013.01);
(Continued)

(58) Field of Classification Search
None
See application file for complete search history.

(56) References Cited

U.S. PATENT DOCUMENTS

| | | |
|---|---|---|
| 5,766,131 A | 6/1998 | Kondo et al. |
| 5,797,841 A | 8/1998 | Delonzor et al. |
| | (Continued) | |

FOREIGN PATENT DOCUMENTS

| | | |
|---|---|---|
| AU | 2003275133 B2 | 4/2004 |
| AU | 2013260649 A1 | 6/2014 |
| | (Continued) | |

OTHER PUBLICATIONS

A. Johansson "A neutral network for photoplethysmographic respiratory rate monitoring", Proc. SPIE, 4434, 2001, p. 109-118.
(Continued)

*Primary Examiner* — Eric F Winakur
*Assistant Examiner* — Marjan Fardanesh
(74) *Attorney, Agent, or Firm* — Idea Intellectual Limited; Margaret A. Burke; Sam T. Yip

(57) ABSTRACT

The present invention relates to a wearable device for healthcare and method for using the device. More specifically, the wearable device is worn on a finger for measuring the health data of the user, selected from one or more of heart rate, blood oxygen saturation, heart rate variability. Based on the measured data, the sleep quality can be monitored and recorded. Disorders such as obstructive sleep apnea (OSA), can be detected. The wearable device may include an optical sensor coupled with or embedded in a main body including a visible light emitter, an IR light emitter and a light detector being arranged along a longitudinal direction of the finger. During operation of the wearable device, the heart rate is monitored based on a detected light signal. When the heart
(Continued)

rate is higher than an adaptive threshold, both heart rate and blood oxygen saturation are monitored.

20 Claims, 18 Drawing Sheets

(51) Int. Cl.
    *A61B 5/0205* (2006.01)
    *A61B 5/024* (2006.01)
(52) U.S. Cl.
    CPC ........ *A61B 5/02438* (2013.01); *A61B 5/1455* (2013.01); *A61B 5/02055* (2013.01); *A61B 5/02405* (2013.01); *A61B 5/4815* (2013.01); *A61B 5/746* (2013.01)

(56) References Cited

U.S. PATENT DOCUMENTS

| | | | |
|---|---|---|---|
| 5,891,023 | A | 4/1999 | Lynn |
| 5,906,582 | A | 5/1999 | Kondo et al. |
| 5,964,701 | A | 10/1999 | Asada et al. |
| 6,198,951 | B1 | 3/2001 | Kosuda et al. |
| 6,223,064 | B1 | 4/2001 | Lynn |
| 6,322,515 | B1 | 11/2001 | Goor et al. |
| 6,402,690 | B1 | 6/2002 | Rhee et al. |
| 6,580,944 | B1 | 6/2003 | Katz et al. |
| 6,608,562 | B1 | 8/2003 | Kimura et al. |
| 6,699,199 | B2 | 3/2004 | Asada et al. |
| 6,856,829 | B2 | 2/2005 | Ohsaki et al. |
| 7,041,049 | B1 | 5/2006 | Raniere |
| 7,309,314 | B2 | 12/2007 | Grant et al. |
| 7,477,924 | B2 | 1/2009 | Chin |
| 7,483,731 | B2 | 1/2009 | Hoarau et al. |
| 7,522,948 | B2 | 4/2009 | Chin |
| 7,650,177 | B2 | 1/2010 | Hoarau et al. |
| 7,674,230 | B2 | 3/2010 | Reisfeld |
| 7,676,253 | B2 | 3/2010 | Raridan, Jr. |
| 7,693,559 | B2 | 4/2010 | Raridan et al. |
| 7,869,849 | B2 * | 1/2011 | Ollerdessen ....... A61B 5/14552 600/323 |
| 7,881,762 | B2 | 2/2011 | Kling et al. |
| 8,145,288 | B2 | 3/2012 | Baker, Jr. |
| 8,172,766 | B1 | 5/2012 | Kayyali et al. |
| 8,260,391 | B2 | 9/2012 | Hoarau |
| 8,352,010 | B2 | 1/2013 | Matlock |
| 8,417,309 | B2 | 4/2013 | Price |
| 8,419,649 | B2 | 4/2013 | Banet et al. |
| 8,437,824 | B2 | 5/2013 | Moon et al. |
| 8,506,480 | B2 | 8/2013 | Banet et al. |
| 8,515,515 | B2 | 8/2013 | McKenna et al. |
| 8,562,526 | B2 | 10/2013 | Heneghan et al. |
| 8,679,012 | B1 | 3/2014 | Kayyali |
| 8,700,116 | B2 | 4/2014 | Schlottau et al. |
| 8,758,243 | B2 | 6/2014 | Wang et al. |
| 8,781,753 | B2 | 7/2014 | Ochs et al. |
| 8,862,195 | B2 | 10/2014 | Hornero Sanchez et al. |
| 8,888,720 | B2 | 11/2014 | Hudson |
| 8,920,331 | B2 | 12/2014 | Ouchi et al. |
| 8,989,831 | B2 | 3/2015 | Al-Ali et al. |
| 9,107,635 | B2 | 8/2015 | Ochs et al. |
| 9,220,410 | B2 | 12/2015 | Sheynblat et al. |
| 9,241,643 | B2 | 1/2016 | Lisogurski et al. |
| 9,241,676 | B2 | 1/2016 | Lisogurski et al. |
| 9,386,951 | B2 | 7/2016 | Sanchez et al. |
| 2002/0029000 | A1 | 3/2002 | Ohsaki et al. |
| 2004/0113771 | A1 | 6/2004 | Ozaki et al. |
| 2007/0078309 | A1 | 4/2007 | Matlock |
| 2007/0123756 | A1 * | 5/2007 | Kitajima ............ A61B 5/14552 600/300 |
| 2007/0213620 | A1 | 9/2007 | Reisfeld |
| 2007/0213621 | A1 | 9/2007 | Reisfeld et al. |
| 2007/0213622 | A1 | 9/2007 | Reisfeld |
| 2008/0171915 | A1 | 7/2008 | Kawajiri et al. |
| 2009/0018454 | A1 | 1/2009 | Hung |
| 2010/0130875 | A1 | 5/2010 | Banet et al. |
| 2011/0213217 | A1 | 9/2011 | McKenna et al. |
| 2012/0116193 | A1 | 5/2012 | Huang |
| 2012/0130203 | A1 | 5/2012 | Stergiou et al. |
| 2012/0150047 | A1 | 6/2012 | Terumoto et al. |
| 2012/0179011 | A1 | 6/2012 | Moon et al. |
| 2013/0046151 | A1 * | 2/2013 | Bsoul ................. A61B 5/4815 600/301 |
| 2013/0046159 | A1 | 2/2013 | Mccombie et al. |
| 2013/0096405 | A1 | 4/2013 | Garfio |
| 2013/0253332 | A1 | 9/2013 | Hayman et al. |
| 2014/0276145 | A1 | 9/2014 | Banet et al. |
| 2014/0336517 | A1 | 11/2014 | Schnall et al. |
| 2015/0112158 | A1 | 4/2015 | He et al. |
| 2015/0220109 | A1 | 8/2015 | von Badinski et al. |
| 2015/0374310 | A1 | 12/2015 | Lee |
| 2016/0066827 | A1 | 3/2016 | Workman et al. |
| 2016/0166162 | A1 | 6/2016 | Yamaji et al. |
| 2016/0317060 | A1 | 11/2016 | Connor |

FOREIGN PATENT DOCUMENTS

| | | |
|---|---|---|
| CN | 202740006 U | 2/2013 |
| CN | 103156594 A | 6/2013 |
| CN | 103892796 A | 7/2014 |
| CN | 104720746 A | 6/2015 |
| CN | 204468058 U | 7/2015 |
| EP | 0773504 A1 | 5/1997 |
| EP | 2497416 B1 | 4/2014 |
| EP | 2883497 A1 | 6/2015 |
| GB | 2516220 A | 1/2015 |
| GB | 2537818 A | 11/2016 |
| JP | H04215742 A | 8/1992 |
| JP | 2002028139 A | 1/2002 |
| JP | 2002224088 A | 8/2002 |
| JP | 2004041482 A | 2/2004 |
| JP | 2004351107 A | 12/2004 |
| JP | 2005110816 A | 4/2005 |
| JP | 2006204742 A | 8/2006 |
| JP | 3820162 B2 | 9/2006 |
| JP | 2006288663 A | 10/2006 |
| JP | 2007105316 A | 4/2007 |
| JP | 2007117641 A | 5/2007 |
| JP | 2007330638 A | 12/2007 |
| JP | 2009082660 A | 4/2009 |
| JP | 2009153550 A | 7/2009 |
| JP | 4385677 B2 | 12/2009 |
| JP | 4433756 B2 | 3/2010 |
| JP | 4549900 B2 | 9/2010 |
| JP | 4710084 B2 | 6/2011 |
| JP | 4739126 B2 | 8/2011 |
| JP | 2013220312 A | 10/2013 |
| JP | 2014108141 A | 6/2014 |
| JP | 5682369 B2 | 3/2015 |
| JP | 5760351 B2 | 8/2015 |
| JP | 2015178011 A | 10/2015 |
| WO | 2014167457 A1 | 10/2014 |
| WO | 2015159693 A1 | 10/2015 |

OTHER PUBLICATIONS

Ali A. El-Solh et. al., "Validity of neutral network in sleep apnea", Sleep, 22, 1999, p. 105-111.
International Search Report of PCT/CN2017/083636 dated Jul. 27, 2017.
Office Action issued in corresponding China patent application No. 201780000415.0 dated Jul. 14, 2020.
Sobhan Salari Shahrbabaki et al., "Pulse Transit Time and Heart Rate Variability in Sleep Staging", 2016 38th Annual International Conference of the IEEE Engineering in Medicine and Biology Society, p. 3467-3472.
European Search Report of corresponding European Patent Application No. 17795533.3 dated Sep. 18, 2020.
Office action of corresponding Taiwan Patent Application No. 106115339 dated Feb. 1, 2018.

(56) References Cited

OTHER PUBLICATIONS

Office action of corresponding Taiwan Patent Application No. 106115339 dated May 23, 2018.
Office action of corresponding Taiwan Patent Application No. 106115339 dated Dec. 6, 2018.
Office action of corresponding Taiwan Patent Application No. 106115339 dated Nov. 27, 2019.
Office action of corresponding Taiwan Patent Application No. 106115339 dated Mar. 19, 2020.
European search report of corresponding European Patent Application No. 17795533.3 dated Nov. 11, 2019.
First office action of corresponding China Patent Application No. 201780000415.0 dated Jan. 19, 2020.

* cited by examiner

WEARABLE DEVICE FOR HEALTHCARE AND METHOD THEREOF

CROSS REFERENCE TO RELATED APPLICATION

The present application is a national phase application of PCT/CN2017/083636 filed on May 9, 2017 which claims priority to the U.S. Provisional Application Nos. 62/333,785 filed 9 May 2016 and 62/365,978 filed 22 Jul. 2016; the disclosures of which are incorporated herein by reference in their entirety.

FIELD OF INVENTION

This invention relates generally to a device, method and system for monitoring a user's health status.

BACKGROUND

Currently technology integrated with various health tools is becoming a very popular trend within the healthcare industry and is increasingly being used on a more regular basis. Wearable devices are one such category of technology. Many of the wearable devices that are providing a plethora of health data that can be used to inform both personal and clinical decisions for consumers utilize the growing roster of available tools. Generally, wearable devices with health tools can measure the heart rate (HR), heart rate variability (HRV), blood oxygen saturation, temperature, motion, and/or other biological information of the user via noninvasive methods.

In one main application field, health tools are integrated into a smart watch or bracelet. However, the smart watch or bracelet is bulky and thus may be uncomfortable for long term wearing. In another application field, a pulse oximeter can be used to measure health data of the user at the fingertip. Compared to the smart-watch and/or bracelet, the pulse oximeter, being worn on the fingertip, is lighter. However, it is inconvenient and not stable for long-term wear on the fingertip, especially during sleep.

As such, there is a need for a healthcare device to be used for an extended period of time for health data measurements and monitoring status of the user without causing any inconvenience or discomfort to the user.

BRIEF DESCRIPTION OF THE DRAWINGS

Advantages of the present invention will be apparent from the following detailed description of exemplary embodiments thereof, which description should be considered in conjunction with the accompanying drawings, in which.

SUMMARY OF THE INVENTION

Figure 1:
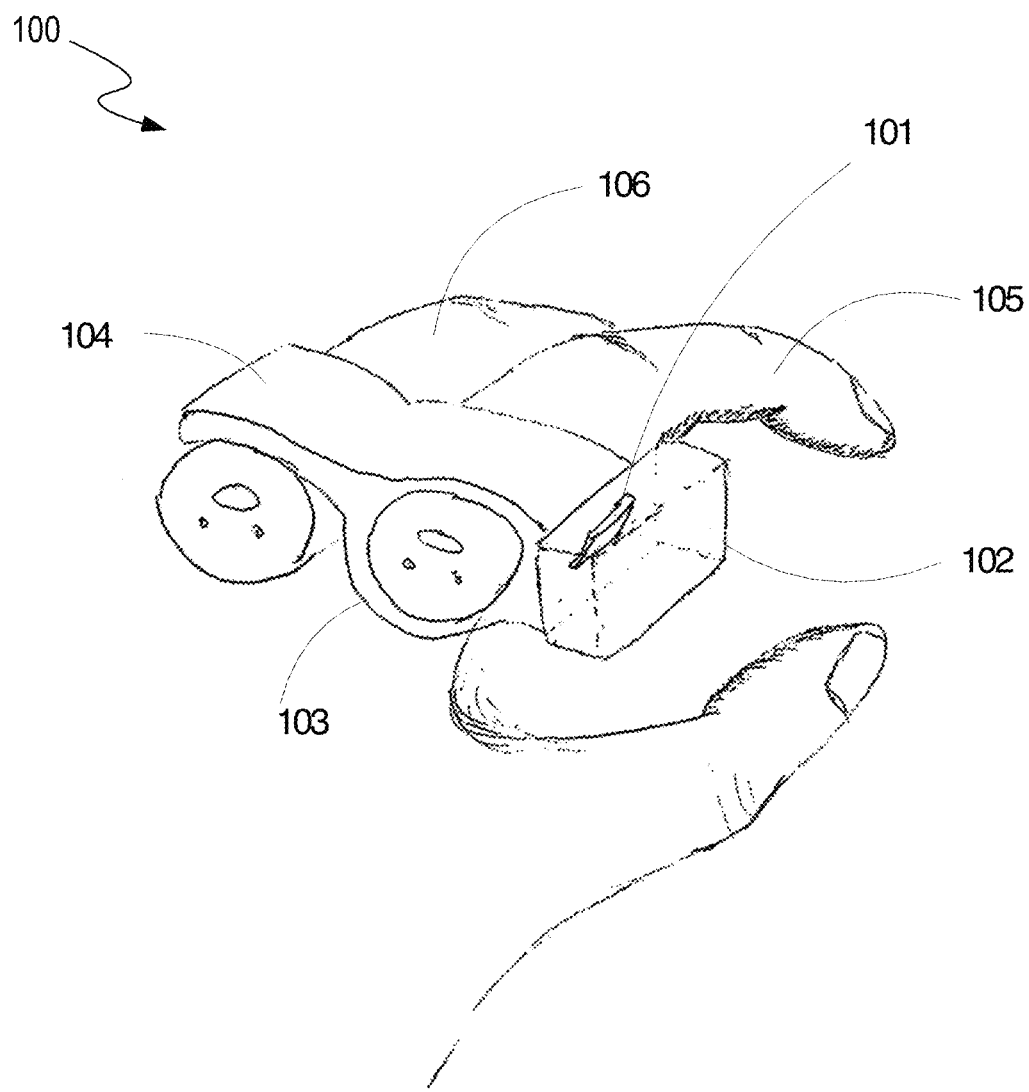
FIG. 1 illustrates a schematic drawing of a wearable device 100, according to one embodiment.

The present invention relates to a wearable device for healthcare and method thereof. More specifically, the wearable device is worn on a finger for measuring the health data of the user, including but not limited to, heart rate, blood oxygen saturation, etc. Based on the measured data, the sleeping quality and disorder condition, e.g., obstructive sleep apnea (OSA), can be monitored and recorded.

In one embodiment, an electronic device for a user comprises a first light emitter for emitting a first light to a digit of the user; a second light emitter for emitting a second light to the digit; and a light detector for detecting the first and second light reflected from the digit, wherein the first and second light emitters and the light detector are arranged substantially along a longitudinal direction of the digit.

In another embodiment, a wearable device for detecting physiological information of a user comprises a main body configured to be at least partially worn on a digit of the user; an optical transducer coupled to or embedded in the main body for detecting the physiological information through a blood vessel of the digit; and a matching unit coupled to the main body and operable for guiding the user to properly wear the wearable device and to reduce the movement of the wearable device.

In another embodiment, a method for detecting physiological information of a user, comprises the steps of detecting a first physiological signal of the user based, at least in part, on a first light reflected from the user, in a first stage; determining whether the first physiological signal has increased higher than a first predetermined threshold, if yes, progressing to a second stage; otherwise returning to the first stage; and detecting the first physiological signal and a second physiological signal based, at least in part, on the first light and a second light reflected from the user, in the second stage.

In another embodiment, a method for waking a user comprises the steps of monitoring a heart rate and heart rate variability of the user; and waking up the user when the detected heart rate and heart rate variability are higher than respective predetermined thresholds.

In another embodiment, a wearable system assembly for a user, comprises a wearable device for detecting physiological information of the user, comprising: first and second light emitters for respectively emitting first and second light to a digit of the user; a light detector for detecting the first and second light reflected from the digit, wherein the first and second light emitters and the light detection are arranged substantially along a longitudinal direction of the digit; and a docking station for storing and charging the wearable device.

In another embodiment, an application system for a user comprises an electronic device for detecting physiological information of the user; one or more functional nodes, comprising sensor, database, entertainment, and/or social network; and a base server for communicating with the wearable device and the functional nodes via wireless or wired transmission for data collection and analysis.

DETAILED DESCRIPTION

Reference will now be made in detail to the embodiments of the present invention. While the invention will be described in conjunction with these embodiments, it will be understood that they are not intended to limit the invention. The invention includes alternatives, modifications and equivalents covered within the scope of the appended claims.

Furthermore, in the following detailed description of the present invention, numerous specific details are set forth in order to provide a thorough understanding of the present invention. However, it will be recognized by one of ordinary skill in the art that the present invention may be practiced without these specific details. In other instances, well known methods, procedures, components, and circuits have not been described in detail as not to unnecessarily obscure aspects of the present invention. In the light of the foregoing background, it is an object of the present invention to provide a wearable device for monitoring health status of the user.

The following embodiments of the present invention describe an exemplary wearable device carried by a user for measuring physiological information of the user. In one embodiment, the wearable device is at least partially worn on a part of the user's body to monitor the health status of the user. In a preferred embodiment, the wearable device is at least partially worn on one or more digits of a limb to measure the physiological information, e.g., heart rate, heart rate variability, blood oxygen saturation, photoplethysmography (PPG) signal, and/or stress, of the user. In one embodiment, a digit of a limb represents, but is not limited to, a digit of a hand and/or a digit of a foot, e.g., a finger of a hand or a toe of a foot (hereinafter, simply referred to as a finger or fingers or a toe or toes). In a preferred embodiment, the wearable device is at least partially worn on a position near the finger root to monitor the user's health information. For example, the wearable device is at least partially worn on a proximal phalange of the finger, in one embodiment. In another preferred embodiment, the wearable device is worn on a user's index finger for easy and comfortable wear.

FIG. 1 illustrates a schematic drawing of a wearable device 100, according to one embodiment. Generally speaking, the wearable device 100 could be any shape as long as it satisfies the requirement of being able to be worn on the finger.

In one embodiment, the wearable device 100 comprises a main body 103 with an open loop in order to suit different sizes of fingers. Furthermore, the wearable device 100 comprises a sensor 101 being attached to the main body 103, and operable for sensing biological information of the user when the wearable device 100 is worn on a digit, e.g., a finger 105, and/or other similar positions of the user through the main body 103. The embodiment of FIG. 1 is for illustration purpose and the structure and wearing manner of the wearable device 100 is not limited to the embodiment. In one embodiment, the sensor 101 is an optical sensor that comprises a first light emitter, a second light emitter and at least one light detector. In one embodiment, the wavelength of the first light generated from the first light emitter is within the range of 850-1000 nm, e.g., IR light, and the wavelength of the second light generated from the second light emitter is within the range of 600-750 nm, e.g., visible light. The first/second light emitter emits the first/second light to a blood vessel in the finger and the light detector is operable to detect the first/second light reflected by the blood vessel in the finger. In one embodiment, the blood vessel may be an artery of the digit, e.g., the princeps pollicis artery which runs along the thumb, the radialis indicis artery which runs along the index finger, and/or the digital arteries which run along the other fingers. The detected first and/or second light signals, that carry health information of the user, is further used to calculate the health data of the user, e.g., a PPG signal, heart rate, heart rate variability, and blood oxygen saturation level, so as to determine the health status of the user. In one embodiment, the heart rate and heart rate variability are determined based on the PPG signal.

In one embodiment, the principle of the sensor 101 for measuring the blood oxygen saturation is based on the first and second light absorption characteristics of oxygenated and deoxygenated hemoglobin. Oxygenated hemoglobin absorbs more first light and allows more second light to pass through. Deoxygenated (or reduced) hemoglobin absorbs more second light and allows more first light to pass through. Based on the first/second light reflected by the blood vessel of the finger 105 and detected by the light detector, the $IN_2/IN_1$ ratio is calculated to determine the blood oxygen saturation, wherein $IN_1$ represents the intensity of the detected first light and $IN_2$ represents the intensity of the detected second light. Furthermore, the heart rate and heart rate variability of the user is able to be detected based on the first light. When the first light is reflected by the blood vessel of the finger 105, the intensity of the reflected first light will vary with the blood volume inside the blood vessel. Therefore, for each heartbeat, the blood volume inside the blood vessel will slightly change thereby altering the intensity of the first light that can be detected by the light detector. As such, the heart rate and heart rate variability can be determined according to the variation of the intensity of the detected first light signal. In an alternative embodiment, the first and second light emitters are integrated into one unit which is able to individually emit the first and second light based on a control signal. The embodiments of the sensor 101 are for illustration purpose and the lighting arrangement, including emitter and detector, is not limited to these embodiments.

Figure 2:
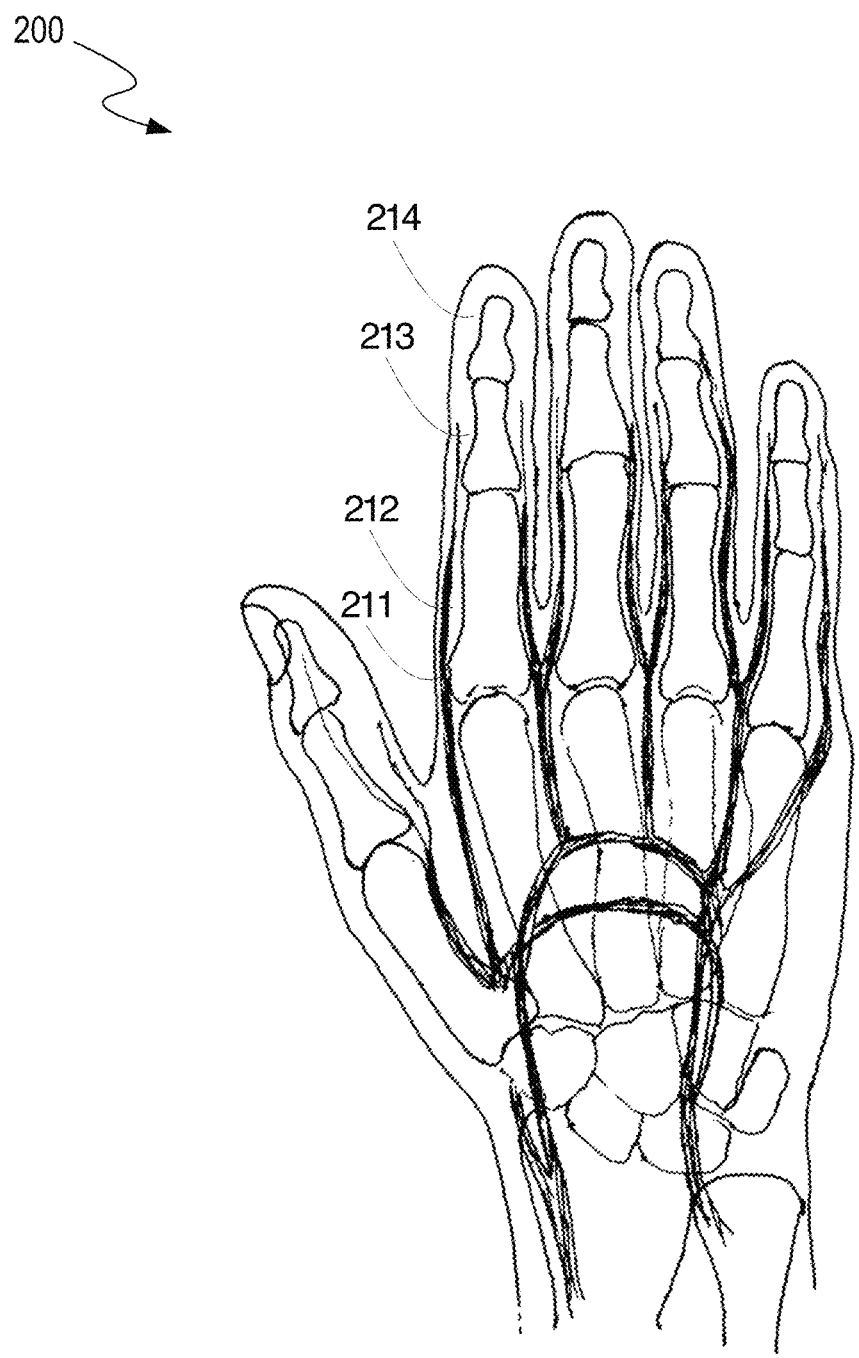
FIG. 2 illustrates a structure of a normal human hand 200.

FIG. 2 illustrates a structure of a normal human hand 200. FIG. 2 is described in combination with FIG. 1. As shown in FIG. 2, the main blood vessel is located near the lateral side of the fingers of the hand 200 with a slight offset to the palmar surface of the fingers. Conventionally, a wearable device is worn on the tip 214 of a finger because plentiful capillaries exist in the fingertip 214, such that the biological information is relatively easily detected. However, as mentioned before, to wear the wearable device on the fingertip is not comfortable, convenient or stable for long-term wear to continuously monitor the subject's health status. Therefore, it is preferred to wear the wearable device 100 on the middle 213 or proximal 212 part of the user's finger for more comfortable, convenient and stable extended wear. However, as compared with the fingertip 214, fewer capillaries exist in the middle or proximal part of the finger. In order to get more physiological information from the blood vessels of the finger, the sensor 101 is preferably positioned near the main blood vessel 211. In one embodiment, the sensor 101 is positioned near an artery of the finger for detecting the health information via the artery. During operation, it is important to fix the sensor 101 of the wearable device 100 close to the main blood vessel 211 to secure the accuracy of the measurement.

Figure 3:
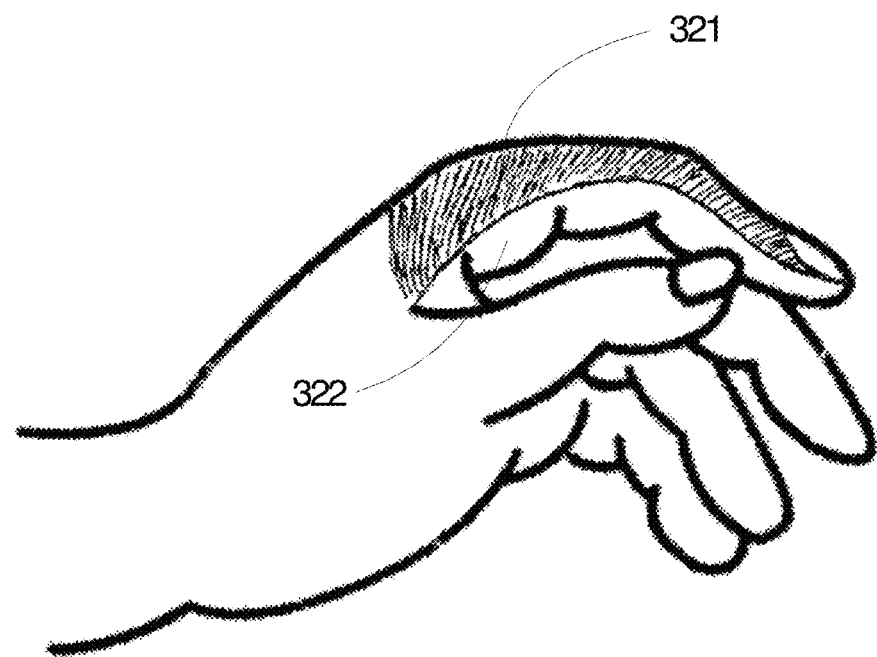
FIG. 3 shows the difference between skin colors of palmar and dorsal surfaces of human hands.

Furthermore, the skin color of the palmar surface 322 is typically lighter than the dorsal surface 321 of human hands, as illustrated in FIG. 3. And among different people, especially for different human races, the skin colors at the dorsal surface 321 of human hands are more variegated as comparing with the palmar surface 322 of hands. As commonly known, melanin is the primary determinant of skin color. The greater the amount of melanin in the skin, the darker the skin color. During operation, the light will be partially absorbed by the melanin of the skin. Further, the light absorption rate will increase with an increasing amount of the melanin in the skin. In other words, more light will be absorbed by darker skin while passing through it. Therefore, on the dorsal surface 321 of the finger, more light is absorbed than that on the palmar surface 322, and the absorption rate varies from person to person. Moreover, the absorption rates of the first light and second light are different due to their different wavelengths. In one embodiment, more second light whose wavelength is within the range of 850-1000 nm is absorbed by the melanin as compared with the first light whose wavelength is within the range of 600-750 nm. As described above, the blood oxygen saturation is calculated based on the first and second light absorption characteristics of oxygenated and deoxygenated hemoglobin. Therefore, due to the uncertain and uneven absorption rates of the first and second light at the dorsal surface 321 due to variations in human skin color, measurement accuracy of the sensor 101 will be significantly affected if positioned on the dorsal surface 321.

Figure 4:
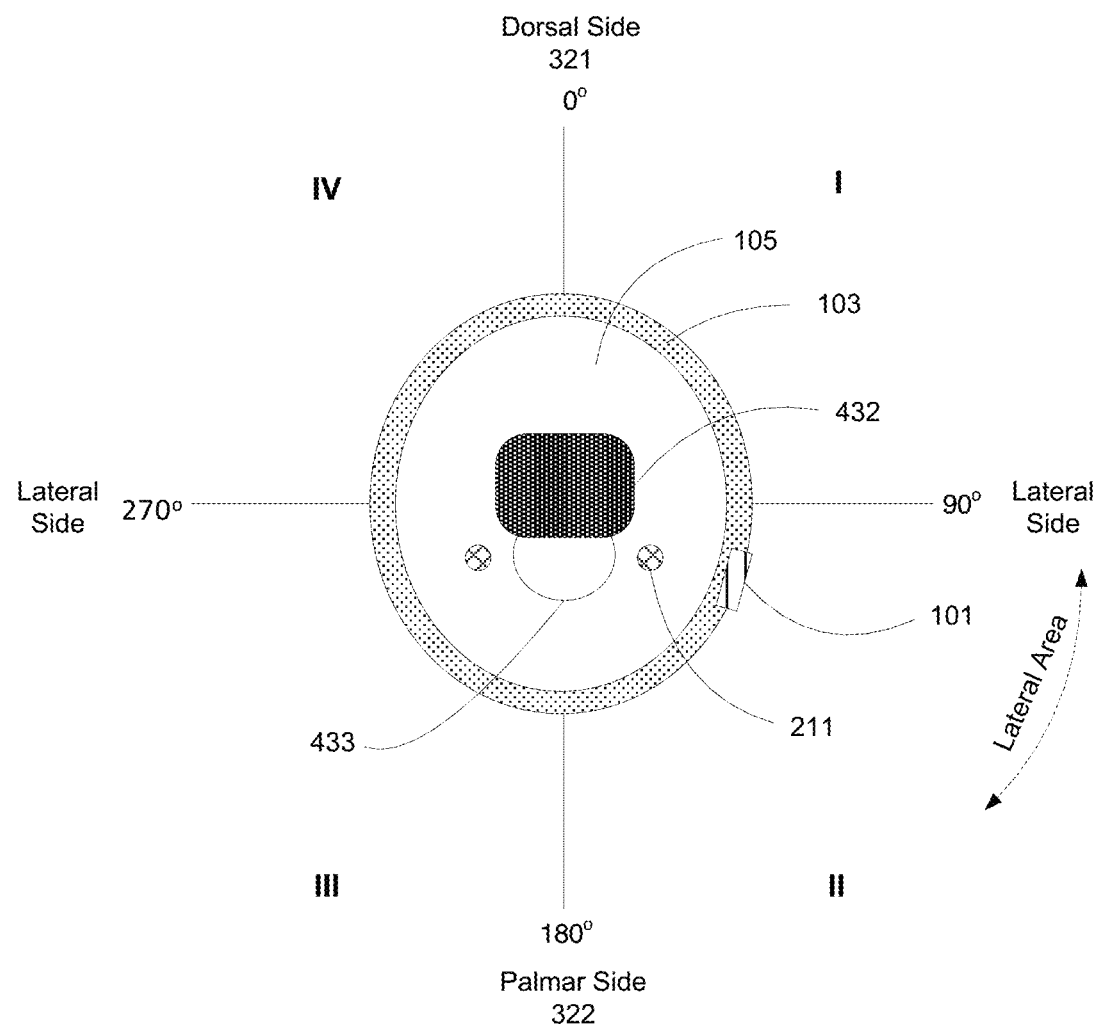
FIG. 4 illustrates the location range of the sensor 101 being arranged on the finger, in accordance with one embodiment of the invention.

In order to enhance the measurement accuracy and reduce the impact on the measurement accuracy as described above, the sensor 101 is preferably placed within a predetermined lateral area of the finger thereby being positioned close to the main blood vessel 211. In one embodiment, the lateral area is an area near the lateral side. In a specified embodiment, the lateral area is located on the palmer surface 322 of the finger and near the lateral side, as exemplarily specified by a circle 323. FIG. 4 illustrates the lateral area of the finger within which the sensor 101 is located, in accordance with one embodiment of the invention. FIG. 4 is described in combination with FIGS. 1-3. As shown in FIG. 4, the finger 105 mainly comprises bone 432, blood vessels including a main blood vessel 211, and tendons 433, wherein the main blood vessel 211 is located near the lateral side with a slight offset to the palmar surface 322. In one embodiment, in order to obtain more information from the main blood vessel 211, the sensor 101 is configured to be positioned adjacent to the palmer surface 322 and under the lateral side of the finger 105 (i.e., area II and/or III of FIG. 4). In a preferred embodiment, an angle range between the edge of the lateral area and the lateral side is from 20 degrees to 50 degrees, as the emitted and reflected light to/from the sensor 101 is closer to the main blood vessel 211.

Figure 5A:
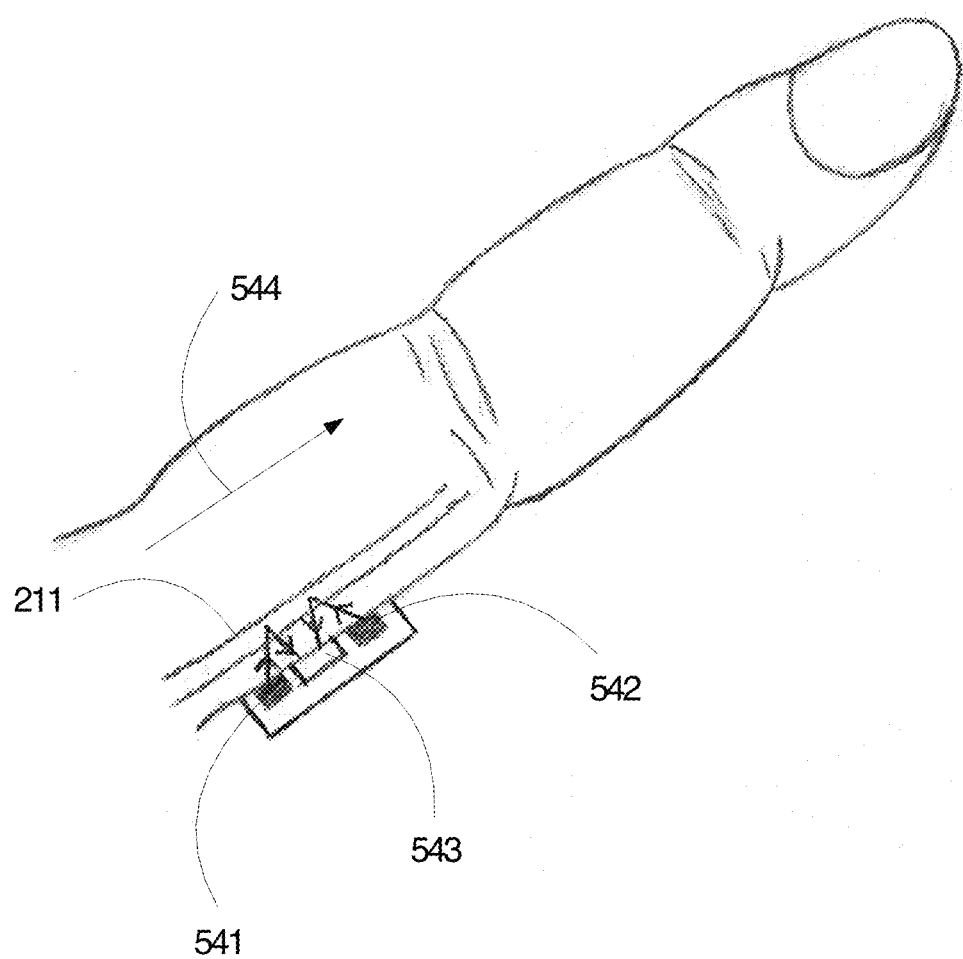
FIG. 5a illustrates a configuration manner of the sensor 101 with respect to a finger, in accordance to one embodiment.
Figure 5B:
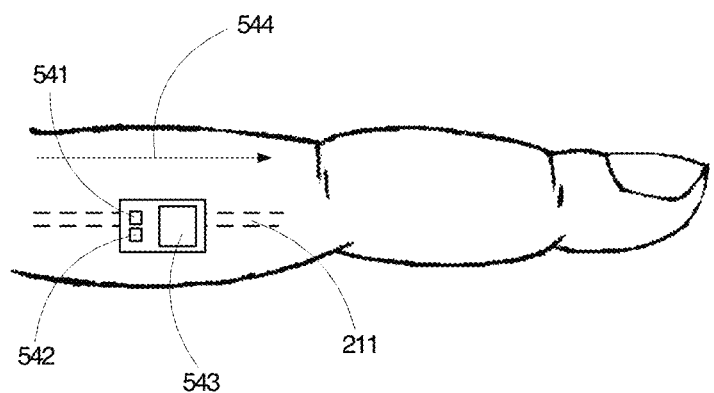
FIG. 5b illustrates another configuration manner of the sensor 101 with respect to a finger, in accordance with an alternative embodiment.

Furthermore, the sensor 101 is preferably placed along a longitudinal direction of the finger in order to minimize the effect on the light passing through the skin caused by uneven skin color along a latitudinal direction of the finger. The longitudinal direction is a direction substantially from finger root to fingertip (or vice versa). The latitudinal direction is substantially perpendicular to the longitudinal direction and extends around the finger. FIG. 5a illustrates a configuration of the sensor 101 with respect to a finger, in accordance with one embodiment. FIG. 5b illustrates another configuration of the sensor 101 with respect to a finger, in accordance with an alternative embodiment. FIGS. 5a and 5b are described in combination with FIGS. 1-4. As shown in FIG. 5a, the sensor 101 is placed along the longitudinal direction 544 of the finger. In a preferred embodiment, the sensor 101 is placed adjacent to the blood vessel 211 at a palmar surface 322 below the lateral side of the finger. More specifically, the sensor 101 comprises first and second light emitters 541 and 542 (or vice versa) and a light detector 543 placed in a linear relationship along the longitudinal direction 544 and close to the blood vessel 211 in order to detect the health information of the user via the blood vessel 211. In a preferred embodiment, the distance between the first light emitter 541 and light detector 543 is substantially the same as the distance between the second light emitter 542 and the light detector 543. Referring to FIG. 5b, since the light emitters 541 and 542 are much smaller than the light detector 543, each of the light emitters 541 and 542 and the light detector 543 are arranged along the longitudinal direction 544 of the finger each light emitter and the light detector being in a linear relationship in the longitudinal direction, wherein the first and second light emitters 541 and 542 are arranged at the same side of the light detector 543 while close to each other. In a preferred embodiment, the distance between the first light emitter 541 and the light detector 543 is substantially the same as the distance between the second light emitter 542 and the light detector 543. As can be understood by one skilled in the art, such details of a wearable device are merely examples, and the claimed subject matter is not so limited. For example, the first and second light emitters 541 and 542 may be arranged at any side of the light detector, and any one of the first and second light emitters 541 and 542 could be arranged above the other one.

Figure 5C:
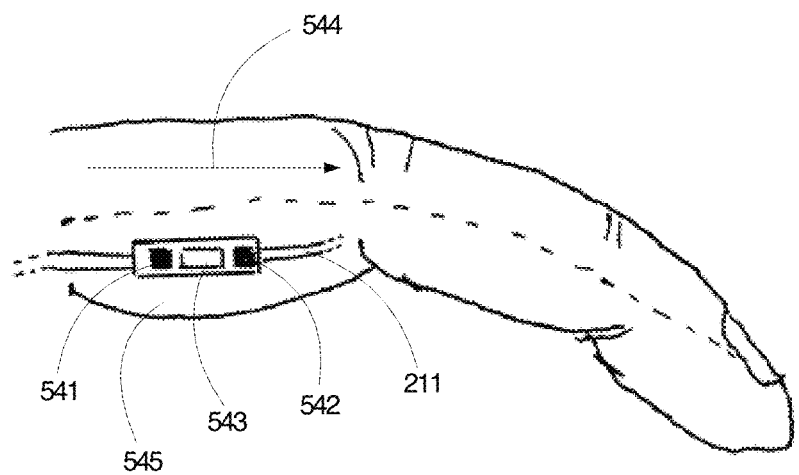
FIG. 5c illustrates less effect on the contact between the sensor 101 and the folded finger, in accordance with one embodiment of the invention.

As mentioned above, the absorption rate of the first and second light is significantly affected by the melanin in the dorsal surface 321 of the finger, which may affect the accuracy of the measurement. With the arrangement illustrated in FIG. 5a, the configuration of the sensor 101 is more compact at one side and the rotation tolerance, within the palmer surface 322, of the sensor 101 around the finger is enhanced. This is due to the light emitter and detector being arranged along the longitudinal direction and at the same level with respect to the latitudinal direction. As compared to the light emitter and detector being arranged along the latitudinal direction, if the sensor 101 rotates around the finger, there is greater tolerance for the light emitter and detector to be kept within the palmer surface during the rotation. Furthermore, since the light emitters and detector 541-543 are arranged along the longitudinal direction 544 at the palmer surface nearby the lateral side, when the finger is folded as shown in FIG. 5c, the impacted palmar surface 545 will not affect the contact between the sensor 101 and the finger skin.

In the embodiment of FIG. 1, the wearable device 100 may further include a matching unit 104 to guide the user to properly wear the wearable device 100 with the sensor 101 being positioned at the target location, and to reduce the rotation of the wearable device 100 around the finger 105 during long-term wear and measurement. In one embodiment, the matching unit 104 comprises at least one extending unit coupled to the main body 103, as shown in FIG. 1. In one embodiment, the extending unit comprises a wing configured at a lateral side of the main body 103. The material of the matching unit 104 may be rigid or elastic, depending upon the desired degree of fixation. When the wearable device 100 is worn on the finger 105, the finger 106 adjacent to the subject finger 105 is coupled with the matching unit 104 that helps to guide the user to properly wear the wearable device 100 and reduce rotation of the wearable device 100. In a preferred embodiment, the wearable device 100 comprises two extending units to hold the adjacent finger 106 for increased stability. The matching unit 104 is designed to correspond to the finger shape for long-term comfortable wear. In an alternative embodiment, the matching unit 104 comprises a loop with or without an opening and coupled to the main body 103. When the wearable device 100 is worn on the finger 105, the loop is configured to surround the adjacent finger 106 to guide the user to properly wear and minimize the rotation of the wearable device 100.

Figure 6A:
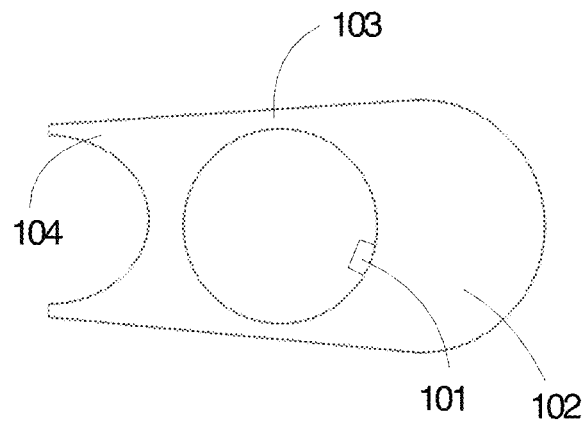
FIG. 6a-c illustrate three types of the wearable device 100 with different shapes of the matching unit 104, according to alternative embodiments.
Figure 6B:
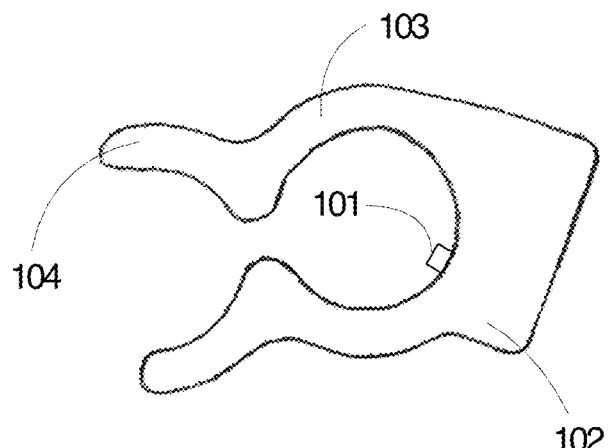
Figure 6C:
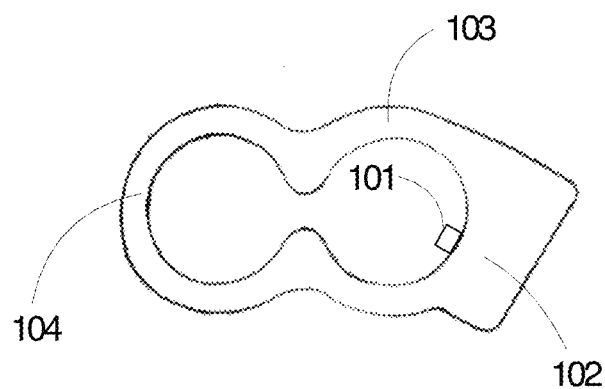

FIGS. 6a-c illustrate three types of the wearable device 100 with different shapes of the matching unit 104, according to alternative embodiments. In FIG. 6a, the matching unit 104 comprises two extending units being symmetrically configured at the lateral side of the main body 103 for coupling with the adjacent finger. In FIG. 6b, the matching unit 104 comprises two extending units being configured at the lateral side of the main body 103 with an offset towards the adjacent finger, in order to fit the shape and structure of the adjacent finger. With such configuration, during the long-term wear of the wearable device 100, especially during sleep, the user will feel more comfortable. In FIG. 6c, the configuration of the matching unit 104 to the main body 103 is similar to FIG. 6b but the matching unit 104 is a loop with or without an opening for coupling with the adjacent finger. As understood by one skilled in the art, the embodiments given in FIGS. 6a-c are examples and not intended to limit the structure and mechanism of the main body 103 and the matching unit 104. In one embodiment, the wearable device 100 further comprises a processing unit coupled with the sensor 101 for data processing. In an alternative embodiment, the sensor 101 is able to communicate with an outside processor or server for data processing via wired or wireless transmission.

In one embodiment, the wearable device 100 includes a functional component 102, as shown in FIG. 1. Optionally the functional component 102 may be detachable such that it may be mounted on and detached from the main body 103 of the wearable device 100. As such, the user may easily replace the main body 103 with another size to fit the fingers of different people while using the same functional component 102. In order to mount the sensor 101 on a proper surface of the finger, i.e., being close to the palmar surface 322 of the finger 105 with a certain offset from the lateral side, i.e., 20 degrees to 50 degrees, the functional component 102 with the sensor 101 attached to the main body 103 is properly configured such that when the wearable device 100 is worn on the user's finger 105, the functional component 102 is close to the lateral side of the finger 105. In one embodiment, the functional component 102 is operable to guide the user to properly wear the wearable device 100 at the proper position. For example, when the wearable device 100 is worn on the index finger and the functional component 102 protrudes toward the thumb, the shape of the functional component 102 is designed to match the shape of the thumb as well as the relationship between the index finger and the thumb, in order to guide the user to properly wear the wearable device 100 at the proper position.

Figure 7:
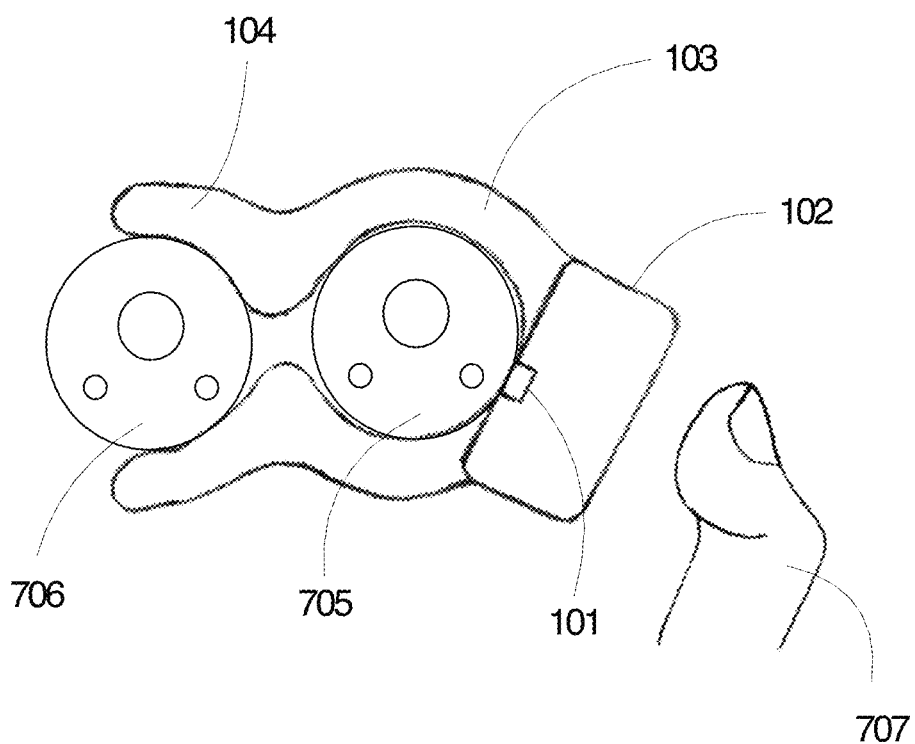
FIG. 7 shows a preferred wearing manner for the wearable device 100, according to one embodiment.

FIG. 7 shows a preferred wearing manner for the wearable device 100, according to one embodiment. FIG. 7 is described in combination with FIG. 1. When wearable device 100 is worn on an index finger 105 via the main body 103, the functional component 102 is placed towards the thumb 707 and the top surface of the functional component 102 is aligned with the lateral side of the thumb 707 for guiding the user to properly wear the wearable device 100 at the proper position. In a preferred embodiment, the wearable device 100 is worn on the proximal phalange of the index finger 705 for easy and comfortable wear. Furthermore, the matching unit 104 is coupled with the adjacent finger 706 in order to align the wearable device 100 to the proper position and reduce the rotation of the wearable device 100 around the index finger 705 during long-term wear and measurement, especially during sleep.

Figure 8A:
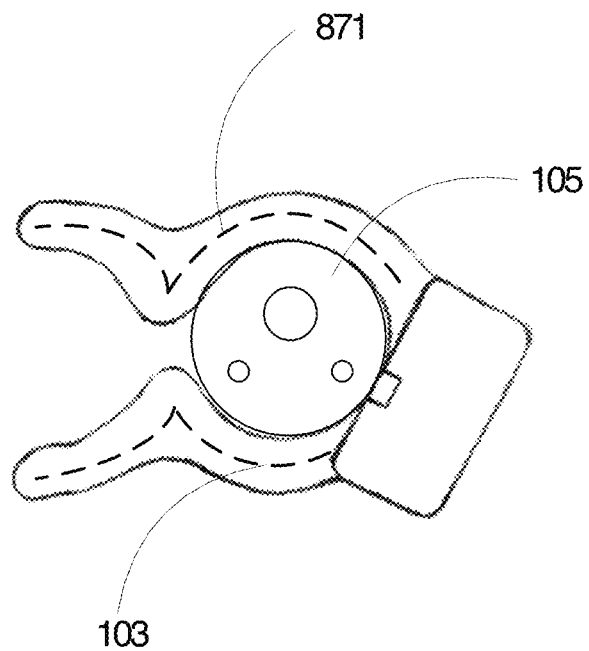
FIG. 8a shows a schematic drawing of a wearable device with a pressure control unit, according to one embodiment.
Figure 8B:
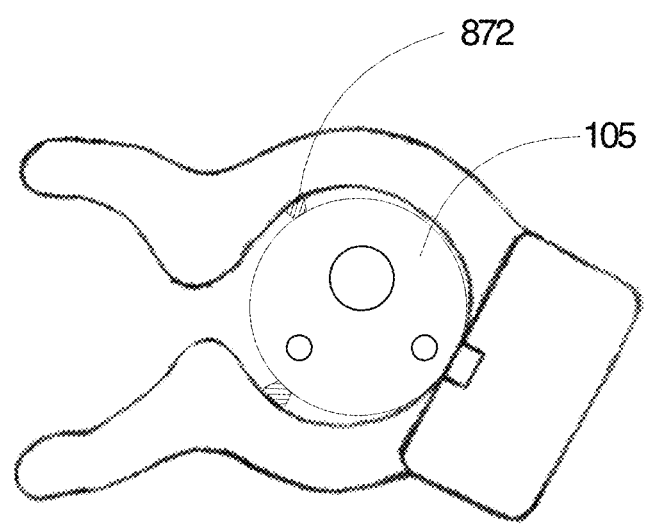
FIG. 8b shows a schematic drawing of a wearable device with another pressure control unit, according to an alternative embodiment.

In one embodiment, the wearable device 100 further comprises a pressure control configuration to control the pressure between the wearable device 100 and the finger. During use, if the wearable device 100 is worn on the finger too tightly, it will block the blood flow and affect the accuracy of measurement. If the wearable device 100 is worn on the finger too loosely, light leakage will occur which may affect the measurement accuracy. FIG. 8a shows a schematic drawing of the wearable device 100 with a pressure control unit, according to one embodiment. FIG. 8b shows a schematic drawing of the wearable device 100 with another pressure control unit, according to an alternative embodiment. FIGS. 8a-b are described in combination with FIG. 1. The embodiments given in FIGS. 8a and 8b are examples and do not limit the structure and mechanism of the pressure control unit. As shown in FIG. 8a, a bendable unit 871 with a predetermined coefficient of deformation is embedded into the main body 103 and/or the matching unit 104 for fitting with different finger sizes. When the wearable device 100 is worn on the finger 105, the bendable unit 871 will provide a clamping pressure within a proper range on the finger 105. As shown in FIG. 8b, one or more protrusions 872 are configured on the inner surface of the main body 103. In one embodiment, at least one protrusion 872 is made by an elastic material. In another embodiment, the main body 103 is, at least partially, made from an elastic material. When the wearable device 100 is worn on the different fingers with different sizes, the wearable device 100 with the protrusion(s) 872 will provide a pressure within a proper range on the finger 105. In other embodiment, the tightness of the wearable device 100 is adjustable and further comprises a pressure sensor to sense the pressure between the wearable device 100 and the finger 105. If the pressure sensor detects the pressure is higher than a first threshold or lower than a second threshold, the tightness of the wearable device 100 will be adjusted automatically or manually by the user.

Figure 9A:
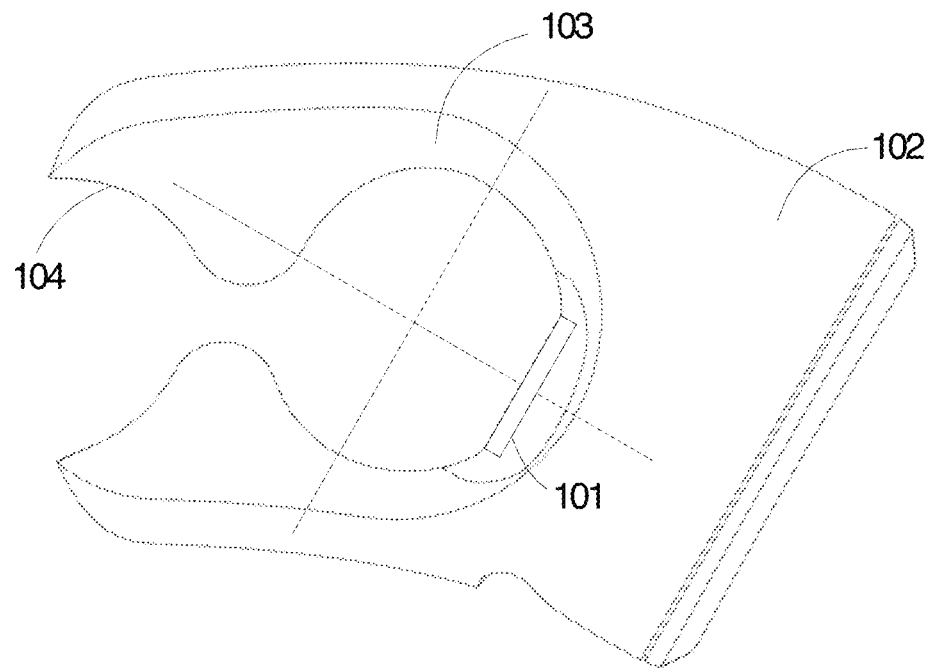
FIGS. 9a and 9b show side views of the wearable device with a pressure control unit, according to one embodiment.
Figure 9B:
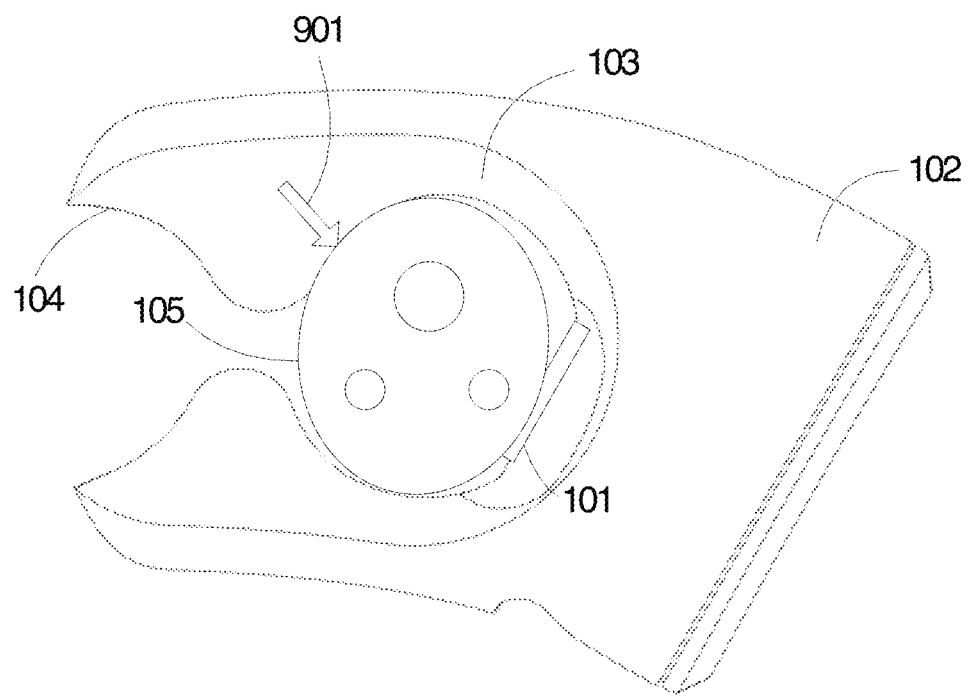

FIG. 9*a* illustrates a schematic drawing of the wearable device 100 with pressure control configuration, according to one embodiment. FIG. 9*b* illustrates how the pressure control works on the finger when the wearable device 100 is worn on the finger, according to the subject embodiment. FIGS. 9*a-b* are described in combination with FIG. 1. As shown in FIG. 9*a*, the main body 103 comprises a loop structure configured such that a force is generated to press the finger against the sensor 101 when the wearable device 100 is worn on the finger.

Furthermore, different from the conventional pulse oximeter worn on the fingertip, the wearable device 100 is designed to be worn on a base of the finger. Since the space between the bases of two fingers are much smaller than that between the fingertips, the shape of the main body 103 may be designed to generate a force on the finger towards the sensor 101 while not affecting the movement of the adjacent fingers, when the wearable device 100 is worn on the finger. In one preferred embodiment, the main body 103 is made of deformable materials and the loop structure of the main body 103 is in an ellipse shape with an axis being arranged in a predetermined direction in order to generate the target force on the finger towards the sensor 101 when the wearable device 100 is worn on the finger. In a more specific embodiment, the axis of the ellipse shape of the loop structure passes through the sensor 101.

When a finger is inserted into the main body 103 of the wearable device 100 as shown in FIG. 9*b*, the special shape of the main body 103 will be slightly distorted against the finger and enable the finger to be attached to the sensor 101. A force 901 as indicated by the arrow is generated on the finger due to the distortion of the main body 103 against the finger. Therefore, the finger is urged to be tightly attached to the sensor 101 so as to avoid the light leakage and prevent the effect of ambient light.

In one embodiment, the functional component 102 is at least partially fabricated from rigid material for supporting and protecting internal functional units, e.g., PCB and sensor 101, while the main body 103 and/or the matching unit 104 are flexible to fit different finger sizes. In one embodiment, for the functional component 102, the rigid layer is disposed inside as a housing of the internal functional units and a flexible layer covers the rigid layer to protect the rigid layer during use.

During the assembly process of the wearable device 100, in one embodiment, the rigid layer of the functional component 102 is formed firstly, and then flexible material is molded on the rigid layer to form the protection layer and is further extended to form the main body 103 and the matching unit 104. Thereafter, the functional units including the sensor 101 are assembled inside the rigid housing and waterproof material is disposed on the edge of the sensor 101. The detecting surface is exposed to the exterior through an aperture in the housing in order to detect the physiological information of the user via the attached finger. Thus, the functional units are sealed in a waterproof manner.

In an alternative embodiment, the outside protection layer of the functional component 102, the main body 103 and the matching unit 104 are initially formed integrally by a flexible material. Afterwards, adhesive material is injected around the internal surface of the protection layer to form the rigid layer as the housing of the functional units. Thereafter, the functional units including the sensor 101 are assembled inside the rigid housing while the detecting surface of the sensor 101 is exposed to the outside through a housing aperture.

In one embodiment, the wearable device 100 further comprises a wireless communication unit operable for transmitting data from the wearable device 100 to an outside device, e.g., a base station server, by way of a wireless radio frequency (RF) link using a proprietary or non-proprietary protocol. In one embodiment, the wireless communication unit comprises a Near Field Communication (NFC) chip for the communication. During operation, when the wearable device 100 is brought close to a certain electronic device, e.g., a smart phone, the electronic device will detect the wearable device 100 via the wireless communication unit and trigger the wearable device 100 to measure the health information of the user via the finger. Furthermore, the wearable device 100 will transfer the measurement result to the electronic device for further processing, recording, and/or display via the wireless communication unit. In one embodiment, the wireless communication unit stores an identification information (ID) of the user and transmits the health information with the user's ID to the electronic device without additional action of inputting user information. In an exemplary embodiment, when an electronic device installed with a specified application (APP) detects the wearable device 100 close to it, the electronic device will trigger the measurement of the wearable device 100 via the APP. The measured health data of the user is then transmitted from the wearable device 100 to the APP for further processing. In one embodiment, the APP will upload the measurement result to a Cloud or a database for further processing.

In one embodiment, a fingerprint authentication unit is integrated in the functional component 102, e.g., to configure a fingerprint authentication function on the main panel of the functional component 102. A person who intends to use the wearable device 100, must pass the fingerprint authentication by pressing a finger, e.g., thumb, onto the main panel of the functional component 102. If the person passes the authentication, he/she will be allowed to access or enable the wearable device 100 for normal measurement.

Figure 10:
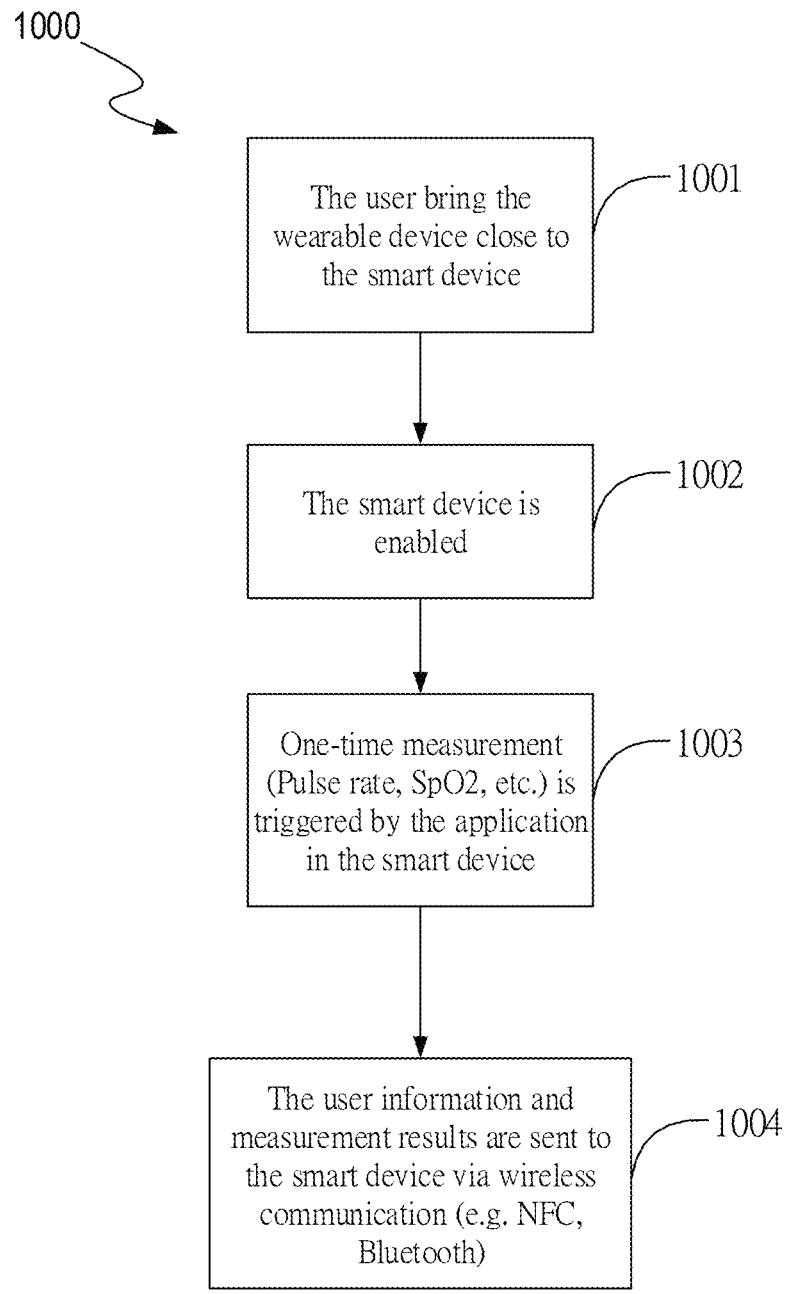
FIG. 10 shows an operation flowchart 1000 of a wearable device with a wireless communication unit, according to one embodiment.

FIG. 10 shows an operation flowchart 1000 of the wearable device 100 with a wireless communication unit, according to one embodiment. FIG. 10 is described in combination with FIG. 1. During the operation, when the user brings the wearable device 100 close to an electronic device, e.g., when the user wearing the wearable device 100 holds up a smart phone, in step 1001, the electronic device is enabled for further processing in step 1002. Then in following step 1003, the electronic device will trigger the wearable device 100 to measure the health information of the user, e.g., pulse rate and/or PPG signal and/or blood oxygen saturation and/or stress, for one or more times. Finally, the electronic device receives the measured health information with the user ID from the wearable device 100 and displays the measurement result to the user in step 1004. During operation, the electronic device will check whether a previous measurement has been completed for a pre-determined period. If yes, the electronic device will trigger the wearable device 100 to start a next measurement. Otherwise, the electronic device will suspend the trigger until reaching the pre-determined period.

In one embodiment, the wireless communication unit is a passive electronic component with low power consumption. With the communication between the wireless communication unit and the external electronic device, the wearable device 100 is triggered to start the measurement without pressing any button once the wearable device 100 is close to the electronic device. As such, the user interface of the wearable device 100 is simplified especially for elderly users and the power consumption of the wearable device 100 will be reduced. In one embodiment, the wireless communication unit with an electronic key is operable to electronically lock and/or unlock the electronic device.

In one embodiment, the wearable device 100 further comprises a motion sensor to detect the motion of the user. In one embodiment, when the user is awake, the wearable device 100 will be enabled to measure the health data under predetermined conditions for saving power, e.g., triggered by the electronic device once the wearable device approaches it as described above. When the user falls asleep, since many serious symptoms, e.g., obstructive sleep apnea, occur unconsciously during the sleep, the wearable device 100 will enter a continuous measurement mode to continuously monitor the health status of the user. In one embodiment, the motion sensor comprises an accelerometer and/or a gyroscope to detect the movement, posture, and/or orientation of body of the user, e.g., lying on a horizontal plane, standing straight, or how a user's hand is placed. When the wearable device 100 is worn on the finger of the user, the motion sensor will detect whether the user is in a sleeping posture, e.g., lying on a horizontal plane without moving, or still awake, e.g., standing straight or moving. If the motion sensor detects the user is in a sleeping posture without any movement during a predetermined time period, it is determined that the user is asleep and the wearable device 100 will start to continuously measure the heart rate of the user. During sleep, when abnormal symptoms, e.g., obstructive sleep apnea (OSA), occur, the heart rate may suddenly increase and the blood oxygen saturation may accordingly decrease, which will negatively impact the user's health. If a heart rate is detected over a normal threshold $T_{HR}$, the wearable device 100 will start measuring the blood oxygen saturation of the user at once. The normal threshold $T_{HR}$ is set based on the heart rate of the user under normal breathing, e.g., the normal threshold $T_{HR}$ is 10% greater than the average heart rate under normal breathing.

Figure 11:
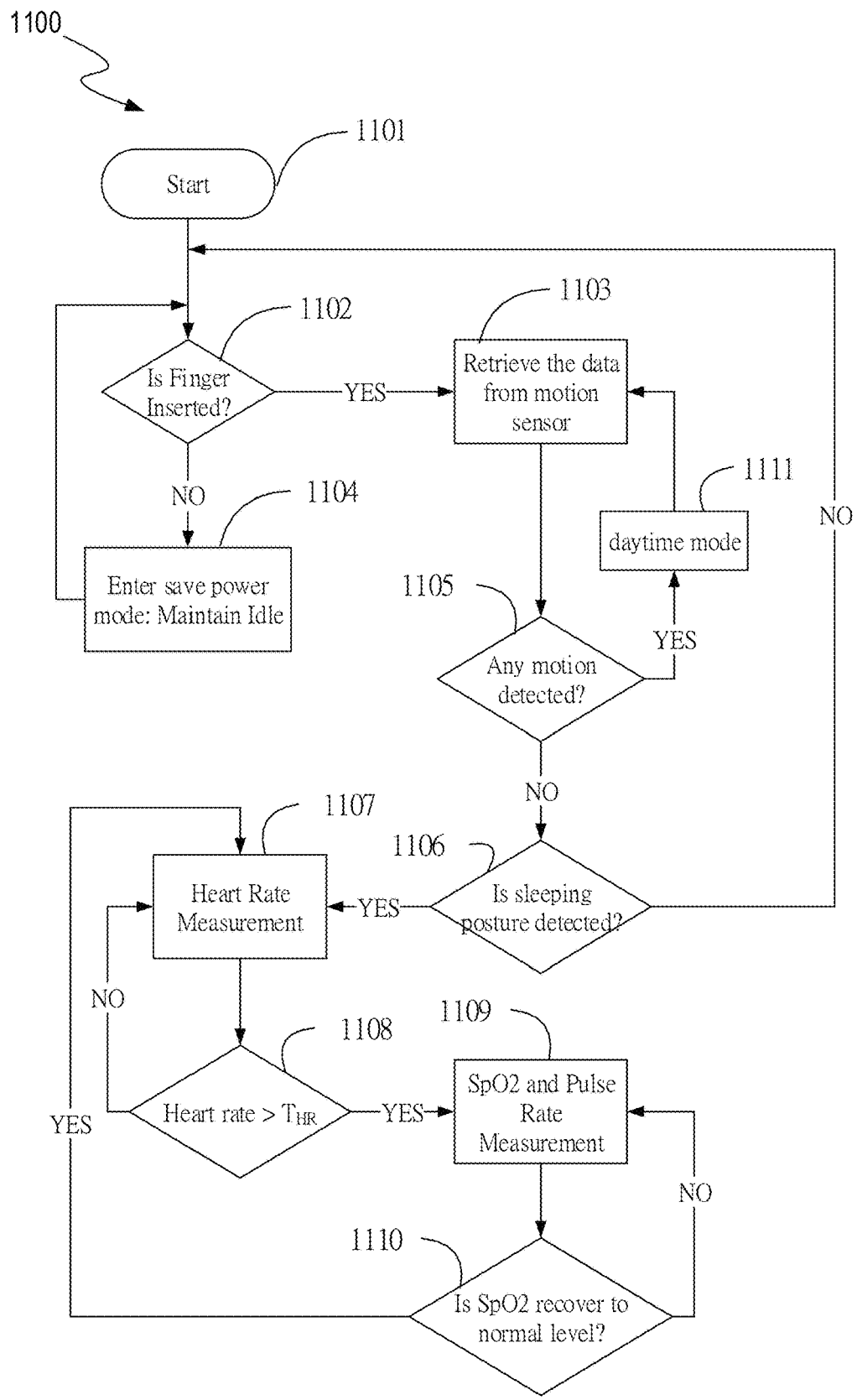
FIG. 11 shows an operation flowchart 1100 of a wearable device, according to one embodiment.

FIG. 11 shows an operation flowchart 1100 of the wearable device 100, according to one embodiment. FIG. 11 is described in combination with FIG. 1. When the wearable device 100 is enabled in step 1101, the wearable device 100 will keep detecting whether a finger is inserted into the wearable device 100 in step 1102. If yes, the wearable device 100 will begin to collect the motion data of the user from the motion sensor in step 1103. Otherwise, the wearable device 100 will remain idle without any measurement in a power-saving mode while maintaining monitoring of the finger insertion in step 1104. After the wearable device 100 collects the motion data from the motion sensor in step 1103, if no movement is detected within a predetermined period in step 1105, the wearable device 100 will further determine whether a sleeping posture is detected in step 1106. Otherwise, the wearable device 100 will enter a daytime mode 1111 to discontinuously measure the health data of the user under certain conditions, e.g., triggered by the outside electronic device, and keep monitoring the movement of the user in step 1103. In step 1106, if the user is detected in a sleeping posture, the wearable device 100 will enter a sleep mode and start continuously measuring and recording the heart rate of the user in step 1107. Otherwise the wearable device 100 will return to step 1102 for detecting whether a finger is inserted into the wearable device 100. During step 1107, if the wearable device 100 detects that the measured heart rate exceeds the normal threshold $T_{HR}$ in step 1108, the wearable device 100 will start to further measure and record the blood oxygen saturation, as well as the heart rate, in step 1109. Otherwise, the wearable device 100 will keep monitoring and recording the heart rate in step 1107. During step 1109, if the measured blood oxygen saturation is higher than a predetermined threshold $T_{BOs}$, that means the blood oxygen saturation has returned to normal level in step 1110, the wearable device 100 will return to step 1107. Otherwise, the wearable device 100 will keep monitoring and recording the blood oxygen saturation and heart rate in step 1109.

With such a configuration, the efficiency of the wearable device 100 will be increased and the power consumption thereof will be reduced. Firstly, the motion sensor is adopted to monitor the posture, body orientation, and/or motion of the user, in order to control the measurement under different conditions to save power. Secondly, the power consumption of the blood oxygen saturation measurement is relatively high when compared with the pulse rate measurement. Since an abnormal condition of the blood oxygen saturation occurs in connection with a sudden increase in the heart rate, the wearable device 100 will start to measure the blood oxygen saturation once the heart rate is higher than the threshold $T_{HR}$, so as to minimize the power consumption.

In one embodiment, the wearable device 100 is operable to determine the sleep cycle of the user based on the measured health information. When people fall asleep, they will experience rapid eye movement (REM) sleep and non-REM sleep through the sleep in various cycles. The beginning stage of the sleep cycle, N1 includes non-REM sleep as it prepares the body to shut down. During this stage, people can be easily awakened by noise or thoughts. The middle stage involves light sleep, N2 usually lasting anywhere for about 10-25 minutes. Non-REM sleep always happens in this stage. Deep sleep, N3 always occurs in a later stage during which activity in the body is low and activity in the brain is very high. REM sleep usually happens in the last stage of the sleep cycle for about 70-90 minutes after a deep sleep phase N3. REM sleep is the stage of sleep when dreaming occurs. When awoken from this stage, a person may feel disoriented. In order to avoid waking up the user during the REM stage, resulting in disoriented condition, it's preferred to wake up the user in a light stage of the sleeping cycle, e.g., in a non-REM stage such as stage N1, to make the user feel more energetic and comfortable.

During operation, when the wearable device 100 detects that respective increments of the heart rate and the heart rate variability of the user are greater than respective predetermined thresholds, it is determined that the user is in the non-REM stage, e.g., stage N1. In order to avoid a disoriented condition caused by waking up the user during the REM stage, the user will be woken up, e.g., by a morning call, when he/she is determined to be in the non-REM stage. In a preferred embodiment, the wearable device 100 further comprises a temperature sensor to detect the user's body temperature. When the wearable device 100 detects the respective increments of the heart rate, heart rate variability and the body temperature of the user are greater than respective predetermined thresholds, it is determined that the user is in a lighter sleep stage. By adding the parameter of the body temperature, the determination of the light sleep stage will be more accurate.

Figure 12:
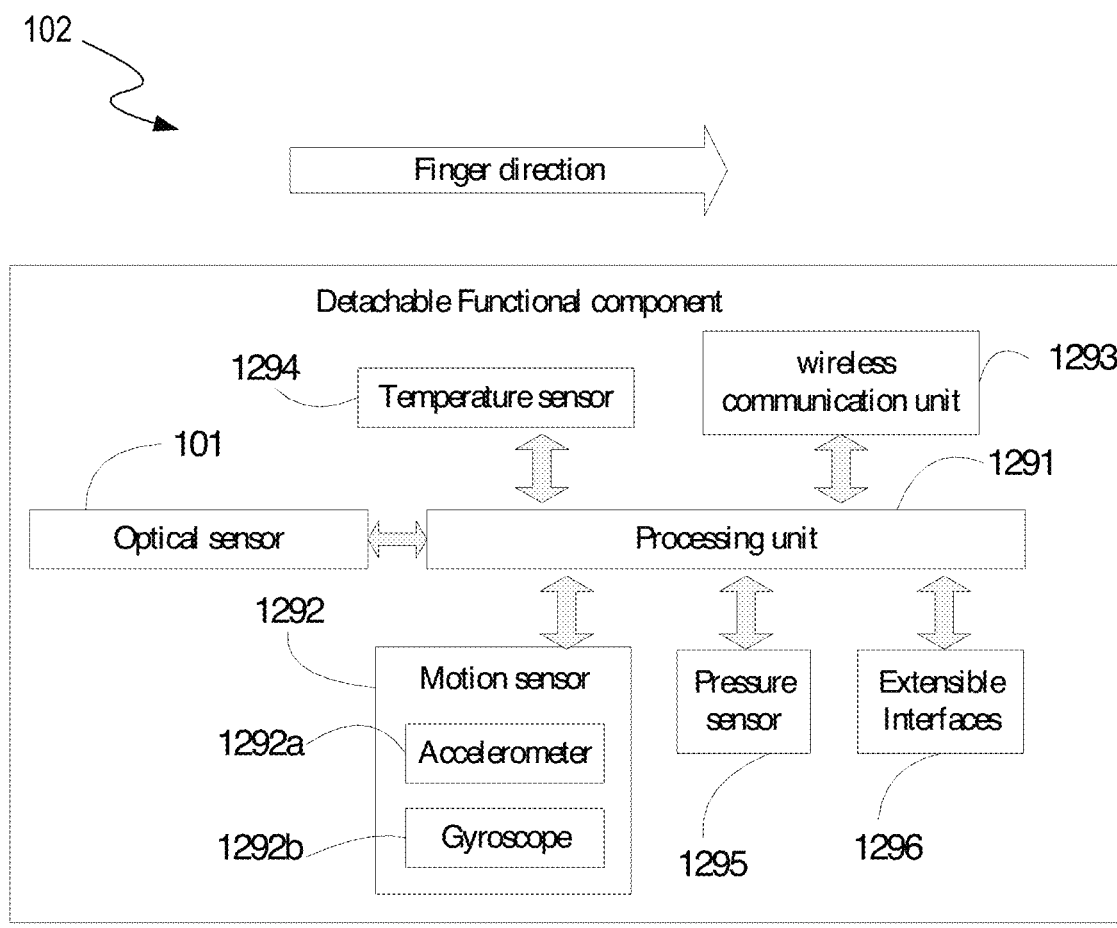
FIG. 12 is a schematic structure of the functional component of a wearable device as described above, according to one embodiment.

FIG. 12 is a schematic structure of the functional component 102 of the wearable device 100 as described above, according to one embodiment. FIG. 12 is described in combination with FIG. 1. As shown in FIG. 12, the functional component 102 comprises the sensor 101 being placed along the longitude direction of the finger, and a processing unit 1291 coupled to the sensor 101 to receive the measured health information of the user for further processing, including, but not limited to, health status analysis, stress analysis, and sleeping quality analysis. In one embodiment, the functional component 102 may further comprises a motion sensor 1292 to detect the movement, body orientation, and/or posture of the user. Based on the detection result from the motion sensor 1292, the processing unit 1291 will decide whether or not to trigger the continuous measurement of the sensor 101. Furthermore, the functional component 102 may comprise a wired or wireless communication unit 1293 for communicating with one or more external electrical devices via wired or wireless transmission, a temperature sensor 1294 to sense the body temperature of the user for healthcare, a pressure sensor 1295 to sense the pressure between the wearable device 100 and the finger for better pressure control, and one or more extensible interfaces 1296 operable to connect with one or more external functional units for function extension. It should be understood to one of ordinary skill in the art that the elements and configuration of the functional component 102 given in FIG. 12 are for illustration purpose and not limited to one embodiment. In other words, the functional component 102 may comprise more or fewer or different functional units and the layout of the functional units is alterable.

Figure 13:
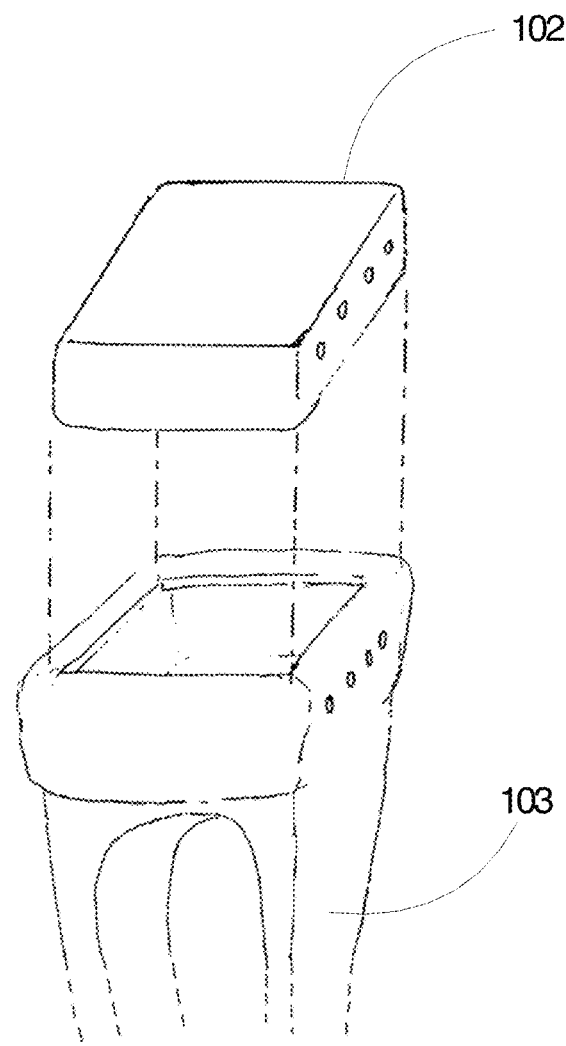
FIG. 13 illustrates a structure of a wearable device with a detachable functional component, according to one exemplary embodiment.

FIG. 13 illustrates a structure of the wearable device 100 with a detachable functional component 102, according to one exemplary embodiment. As shown in FIG. 13, the functional component 102 is able to be detached from and mounted on the main body 103. The main body 103, or further with matching unit 104, are partially omitted with a dashed line and may be any available shape and not limited to the illustration in FIG. 13. With the detachable structure, the user may easily replace the main body 103 from one size to another size to fit the fingers of different people while using the same functional component 102. Furthermore, the detached functional component 102 can be removed, stored, and used for activity tracking in daytime, in one embodiment.

During operation, there are several external functional units operable with the wearable device, e.g., an augmented wireless communication unit, interactive unit, memory, weight scale, spirometer, etc., so that the size of the wearable device may be significantly reduced while supporting various functions. In one embodiment, the wearable device is able to identify which external functional unit is plugged in so as to activate the functionality automatically.

Figure 14A:
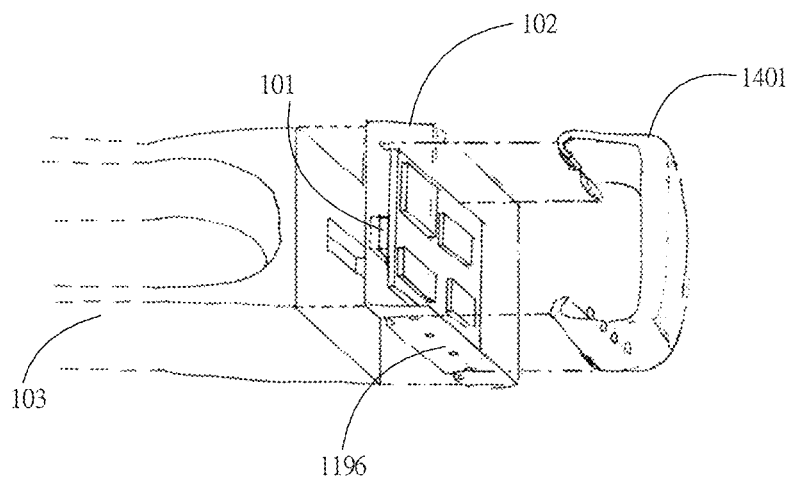
FIG. 14a illustrates a structure of a wearable device with one or more extensible interfaces for extending functionalities, according to one embodiment.

FIG. 14*a* illustrates a structure of the wearable device with one or more extensible interfaces for extending functionalities, according to one embodiment. FIG. 14*a* is described in combination with FIG. 1 and FIG. 12. As shown in FIG. 14*a*, the detachable functional component 102 of the wearable device 100 comprises a sensor 101 and several functional units as illustrated in FIG. 12, which are configured in a predetermined layout. The functional component 102 further comprises one or more extensible interfaces 1296 for receiving one or more external functional units 1401.

In one embodiment, the functional component 102 comprises a plurality of pins for connecting with the external functional units 1401. When one external functional unit 1401 is plugged in the functional component 102, the external functional unit 1401 will connect to a respective set of the pins in a particular manner. For example, for the interactive unit, the 1st and 2nd pins will be connected; for the wireless communication unit, the 3rd and 4th pins will be connected; and for the memory, the 1st and 3rd pins will be connected. By connecting the external functional unit to a respective set of pin(s), the functional component 102 is able to identify the external functional unit 1401 based on the connected pin(s). In an alternative embodiment, when the external functional unit 1401 is plugged into the wearable device 100, the functional component 102 will fetch the identification information in an analog or digital manner from the external functional unit 1401 via the external interface 1296 to identify it. As compared to the previous embodiment of identifying the external functional units 1401 via corresponding pin connection, the configuration of the external interface 1296 in this embodiment is simple and seamless. However, the wearable device 100 may identify the external functional units 1401 quicker in the previous embodiment.

Additionally, similar to FIG. 13, the main body 103, or further with matching unit 104, are partially omitted with a dashed line as they may be any available shape and not limited to the illustration of FIG. 14*a*.

Figure 14B:
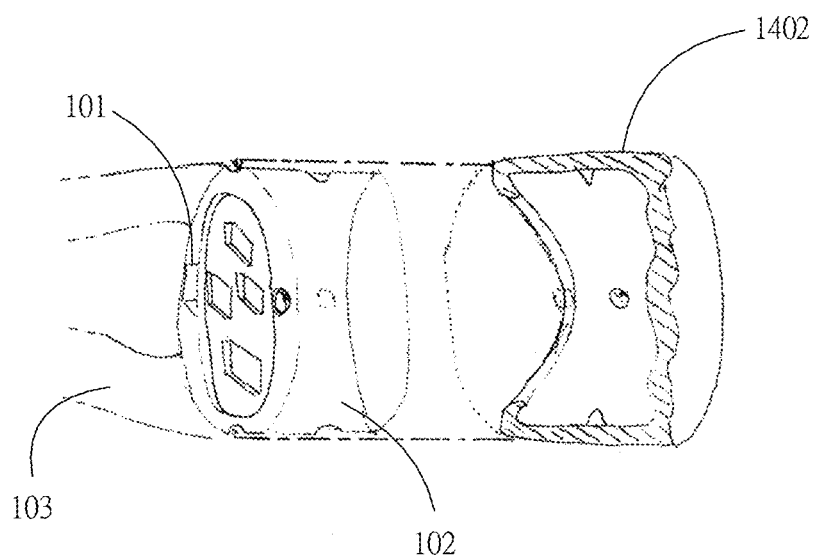
FIG. 14b illustrates a structure of a wearable device with external interface for extending functionalities, according to another embodiment.

FIG. 14*b* illustrates a structure of the wearable device with external interface for extending functionalities, according to another embodiment. FIG. 14*b* is described in combination with FIG. 1 and FIG. 12. As shown in FIG. 14*b*, an external integral functional unit 1402 including several functional sub-units is connectable to the functional component 102 of the wearable device 100. When the external integral function unit 1402 is connected to the functional component 102, the external integral function unit 1402 is configured to activate a target functional sub-unit according to a predetermined manner. In one embodiment, the external integral function unit 1402 is able to rotate at several predetermined angles, e.g., 90, 180, and/or 270 degrees, to enable the corresponding sub-units. With different angular configurations, the functional component 102 will identify which sub-unit is enabled and activate the corresponding sub-unit accordingly. In an alternative embodiment, the external integral functional unit 1202 further comprises a selection panel to select the sub-units and inform the wearable device 100 of the selection.

In one embodiment, a docking station for storing the wearable device 100 is operable for supporting several functions, including but not limited to, a battery charger of the wearable device 100, a portable battery bank being operable for charging not only the wearable device 100 but also other electronics, e.g., smart phone, a wake-up alarm based on the monitoring result of the sleeping cycle by the wearable device 100, an abnormal state alarm for abnormal conditions/symptoms, and/or multi-media player with control based on the monitoring result of the sleeping status of the user. For example, if the wearable device 100 detects the user is in a sleep posture and the heart rate is lower than a sleeping threshold $T_{SLP}$, it is determined that the user is asleep. Then the multi-media player will be turned off for maintaining silence and power saving. The sleeping threshold $T_{SLP}$ is determined based on the heart rate of the user under normal breathing, e.g., the sleep threshold $T_{SLP}$ is 10% smaller than an average heart rate under normal breathing. Furthermore, since the battery of the wearable device 100 is limited due to the compact size, it is important to charge the wearable device 100 periodically. In one embodiment, when the wearable device is stored in the docking station, the wearable device will be charged automatically via the battery charger by the internal battery bank or by outside power. In one embodiment, the docking station is designed to deactivate the wake-up alarm function by putting the wearable device 100 into the docking station for charging, in order to ensure the wearable device 100 is charged by the docking station after long term use during the night. Furthermore, the docking shape is specially designed to help the user to check whether the wearable device 100 is worn on the proper finger in a proper manner.

Figure 15:
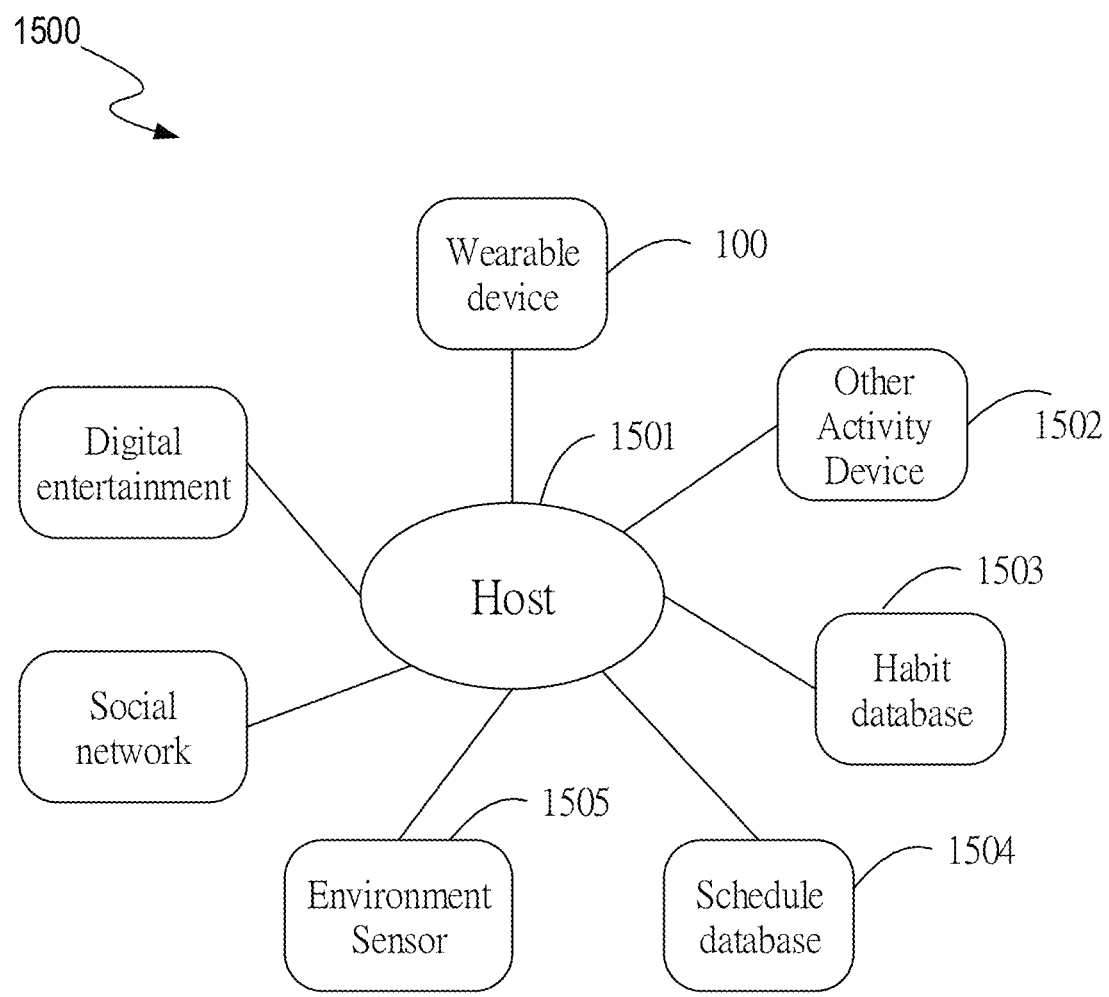
FIG. 15 shows a schematic drawing of an application system 1500 for a wearable device, according to one embodiment.

FIG. 15 shows a schematic drawing of an application system 1500 for the wearable device 100, according to one embodiment. In the application system 1500, the wearable device 100 is able to communicate with a station server 1501 via wired or wireless transmission. During operation, the wearable device 100 transmits the monitoring data to the station server 1501 for further processing, e.g., cloud computing and analysis. The application system 1500 also comprises other functional nodes to get and/or store other data of the subject, e.g., health information from a wristband or other wearable device, habits of the user from the habit database 1503, a schedule list of the user from the schedule database 1504, and/or environment data from the environmental sensor 1505. Based on the data collected, the station server 1501 can perform analysis and provide recommendations/tips to the users.

Figure 16:
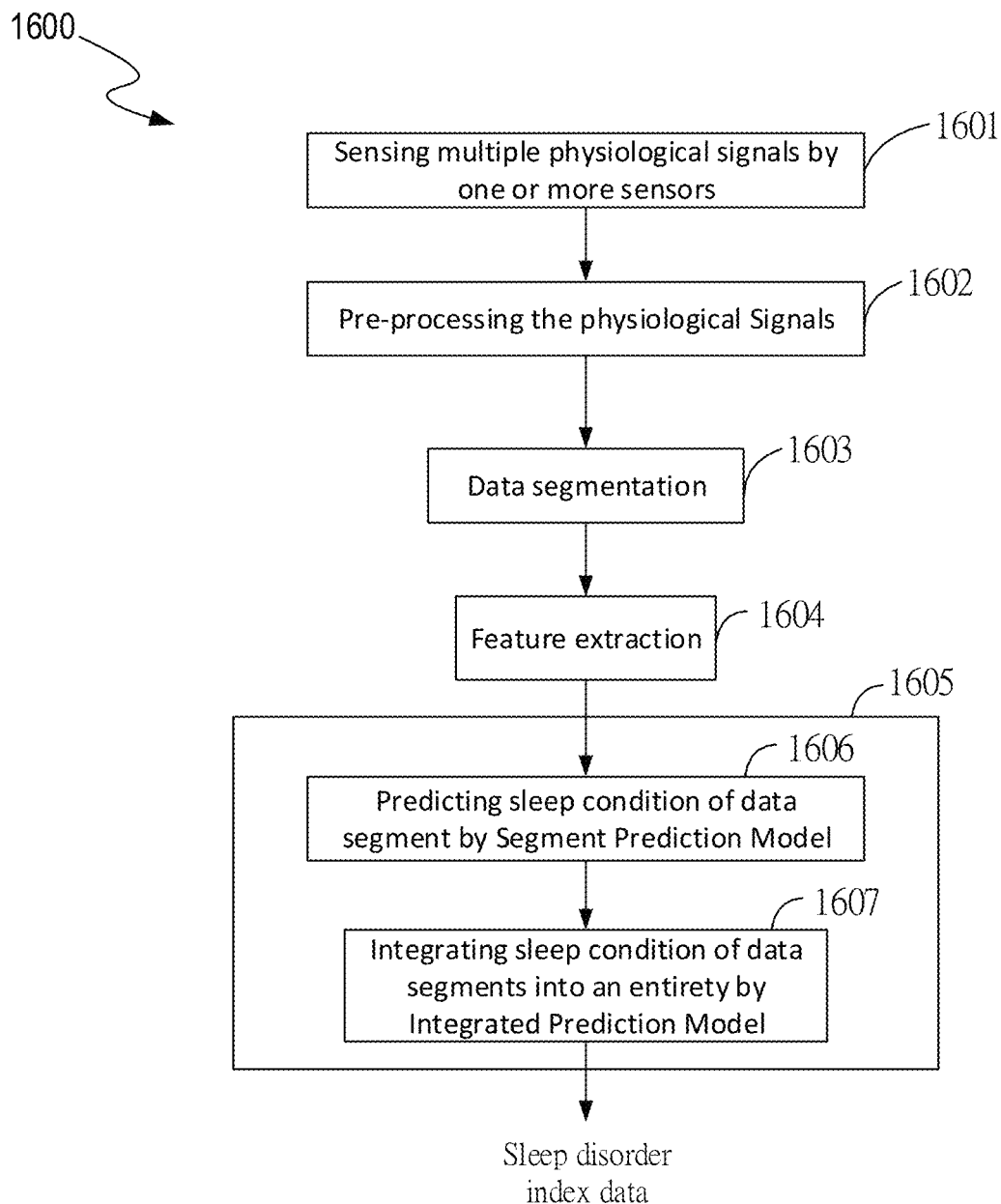
FIG. 16 is a flowchart 1600 for evaluating a sleep condition, according to one embodiment.

Recently, an increasing number of people have a sleep disorder problem during sleep which may seriously interfere with normal physical, mental, social and emotional functioning. Under such condition, it is necessary to monitor and track sleep conditions during the entire period of sleep so as to diagnose and/or prevent serious disease at an early stage. FIG. 16 shows an operation flowchart 1600 for evaluating the sleep condition with the wearable device 100, according to one embodiment. FIG. 16 is described in combination with FIG. 1. The sleep condition may contain occurrences and severities of a sleep disorder and the sleep status.

During operation, multiple physiological signals for evaluating the sleep condition (thereinafter as "evaluation signals") are sensed by one or more sensors in step 1601. In one embodiment, the evaluation signals may include cardiovascular and/or motion signals. In one embodiment, the cardiovascular signals may include, but not limited to, blood oxygen saturation signal (SpO2), SpO2 variations, heart rate, heart rate variations, and/or PPG waveform. In one embodiment, the one or more sensors may include, but are not limited to, the optical sensor and motion sensor of the wearable device 100. In step 1602, the physiological signals are pre-processed by multiple pre-processors. In one embodiment, the pre-processing operations may include, but are not limited to, to filtering, re-calculating, and/or transforming the respective physiological signals. In step 1603, the processed signal data is segmented into several segments. In one embodiment, the processed signal data is time-serially segmented into a sequence of discrete segments. In a preferred embodiment, the processed signal data is divided into shorter segments whose time periods are within a range of 10-30 minutes. In a specific embodiment, the processed signal data is divided into shorter segments of equal time periods. In a more specific embodiment, the processed signal data is divided into multiple segments for every 15-minute time interval. By timely dividing the processed signal data into several shorter segments whose time periods are within 10-30 minutes, the evaluation result of the sleep condition based on the segmented data may be more accurate.

Thereafter, in step 1604, a plurality of features is extracted from the segmented data by analysis. In one embodiment, the features are extracted from the physiological data based on a predetermined feature extraction algorithm to map the physiological data into a reduced set of variables or features to summarize the information in the recording. In one embodiment, the extracted features measure relevant properties of the physiological signals for further evaluation processing. The extracted features are then sent to an evaluation model used to evaluate the sleep condition. More specifically, in one embodiment, the extracted features of the data segments are input into a segment evaluation model to evaluate the occurrences of sleep disorder, e.g., occurrences of hypopnea and apnea, the severities of sleep disorder, e.g., oxygen desaturation levels, and the sleep status, corresponding to each data segment, e.g., the data segment during every 15-mins time interval. Thereafter, the evaluation result of the data segments is sent to an integrated evaluation model to integrate the evaluation result of the data segments into an entirety that indicates sleep conditions over the entire measurement. The evaluated sleep condition will be output as sleep disorder index data, e.g., apnea-hypopnea index and/or oxygen desaturation index, used for further diagnosis.

In one embodiment, the physiological signals of the user measured by the wearable device 100 are sent to the remote host, server, cloud and/or database for recording, analysis and diagnosis based on the evaluation model predefined therein. Furthermore, the evaluation model may be periodically updated with the newly measured signals so as to achieve a more accurate evaluation result.

Figure 17:
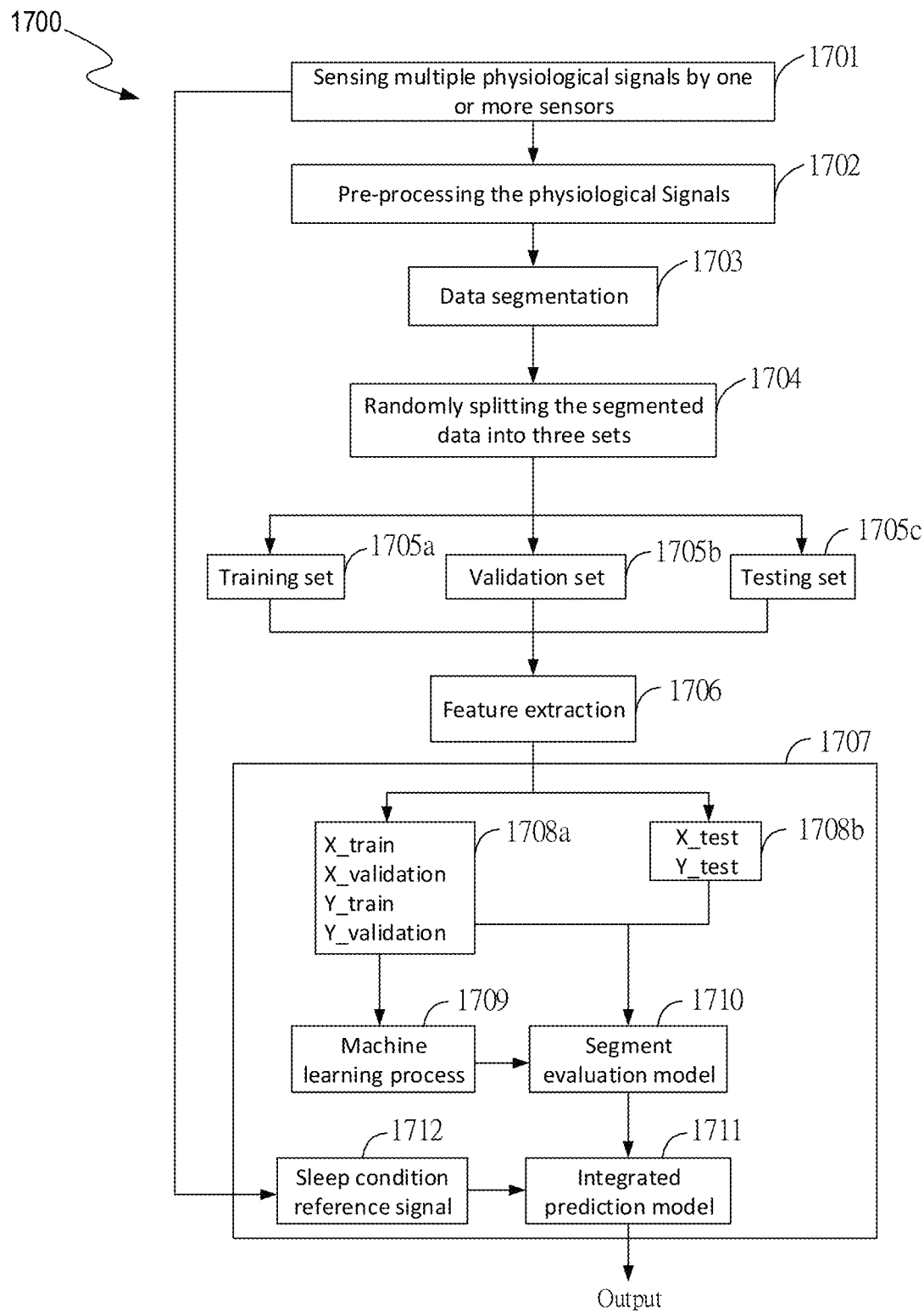
FIG. 17 is a flowchart 1700 of depicting the building of an evaluation model operable for evaluating a sleep condition, according to one embodiment.

FIG. 17 shows an operation flowchart 1700 for building the evaluation model operable for evaluating the sleep condition, in accordance with one embodiment. FIG. 17 is described in combination with FIG. 1 and FIG. 16. During operation, multiple physiological signals are sensed by one or more sensors in step 1701. In one embodiment, the multiple physiological signals may include, but are not limited to, a first group of signals for evaluating the sleep condition, i.e., evaluation signals, and a second group of signals indicating the sleep condition as a reference (thereinafter "reference signals"), wherein the evaluation signals may include the cardiovascular and/or motion signals, and the reference signals may include standard polysomnography signals. The reference signals may include manually and/or automatically labelled annotations of respiratory events and/or sleep status. In one embodiment, the one or more sensors may include, but are not limited to, the wearable device 100 and sensors used in standard polysomnography, e.g. EEG, EMG, EOG, ECG and nasal airflow sensors. In step 1702, the physiological signals are pre-processed by multiple pre-processors. In step 1703, the processed signal data is segmented into several segments.

The segmented data is randomly split into multiple sets, in step 1704. In one embodiment, the segmented data is randomly split into three sets, i.e., a training set 1705*a*, a validation set 1705*b*, and a testing set 1705*c*. In one embodiment, the training set contains 70% of the datasets, while the validation set contains 15% thereof and the testing set contains 15% thereof. Thereafter, in step 1706, a plurality of features is extracted from the data of the three sets by analyzing the subject data. In one embodiment, each set is applied on the same feature extraction algorithm.

In step 1707, an evaluation model used to evaluate the sleep condition is trained and built up based on the extracted features of the three sets. More specifically, features of the training and validation sets in block 1708*a*, i.e. X_training, Y_training, X_validation, and Y_validation are used for a machine learning process to train a machine learning model, e.g. an artificial neural network, in step 1709, with the X_training and X_validation features corresponding to the evaluation signals and Y_training and Y_validation features corresponding to the reference signals. This well-trained machine learning model is the core for building a segment evaluation model in step 1710. The features of a testing set in block 1708*b*, i.e., X_testing and Y_testing, are used to test the performance of the developed segment evaluation model, with the X_testing features corresponding to the evaluation signals and the Y_testing features corresponding to the reference signals. In one embodiment, the output of the segment evaluation model indicates the sleep condition within the corresponding data segment.

Then the integrated evaluation model is developed based on the output of the developed segment evaluation model in step 1711 for integrating the evaluated sleep condition of the data segments into an entirety. The sleep condition reference signals in block 1712 are used to test the performance of the final integrated evaluation model in the step 1711. In one embodiment, the apnea-hypopnea index is the main parameter of reference signals for testing the performance of the integrated evaluation model. The evaluation models, including the segment evaluation model and the integrated evaluation model, are then output and applied to the operation as illustrated in FIG. 16 to evaluate the sleep condition during the entire sleep period.

While the foregoing description and drawings represent embodiments of the present invention, it will be understood that various additions, modifications and substitutions may be made therein without departing from the spirit and scope of the principles of the present invention as defined in the accompanying claims. One skilled in the art will appreciate that the invention may be used with many modifications of form, structure, arrangement, proportions, materials, elements, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims and their legal equivalents, and not limited to the foregoing description.

The invention claimed is:

1. A wearable electronic device for measuring of physiological information of a user, comprising:
   a main body configured to be at least partially worn on an index finger of a hand of the user;
   a functional component coupled to the main body, comprising:
     a first light emitter coupled to the main body for emitting a first light to the index finger of the user;
     a second light emitter coupled to the main body for emitting a second light to the index finger;
     a light detector coupled to the main body for detecting reflected first and second light from the index finger; and
     a matching unit coupled to the main body and comprising an extending unit extending from the main body in an opposing direction to the functional component,
   wherein the first and second light emitters are arranged substantially in a linear relationship with the light detector in a longitudinal direction of the index finger during measuring of physiological information of the user, and the extending unit is configured to be coupled with an adjacent finger to align the device and place the functional component toward the thumb of the hand when worn.

2. The wearable device of claim 1, wherein the matching unit comprises a second extending unit extending from the main body in the opposing direction and configured to be coupled with the adjacent finger and align the device.

3. The wearable device of claim 2, wherein the second extending unit is symmetrically configured to the first extending unit.

4. The wearable electronic device of claim 3, wherein the first and second light emitters are integrated into one component configured to emit the first and second light separately.

5. The wearable electronic device of claim 3, wherein the light emitters and light detector are configured to be located at a palmer surface of the index finger.

6. The wearable electronic device of claim 5, wherein the light emitters and light detector are configured to be positioned adjacent to an artery of the index finger.

7. The wearable electronic device of claim 5, wherein the light emitters and light detector are configured such that when the device is worn, the light emitters and detector are located at the palmer surface with a predetermined offset to a lateral side of the index finger.

8. The wearable electronic device of claim 7, wherein the light emitters and light detector are configured to be located at the palmer surface with an angle offset from 20 degrees to 50 degrees to the lateral side of the index finger.

9. The wearable electronic device of claim 3, wherein a distance between the first light emitter and the light detector is substantially the same as the distance between the second light emitter and the light detector.

10. The wearable electronic device of claim 3 wherein the light detector is configured to sense multiple physiological signals and communicates with a processor to:
    segment the physiological signals into several data segments;
    extract features of the data segments;
    evaluate a sleep condition based on the extracted features of the data segments by a segment evaluation model; and
    integrate the evaluated sleep condition of the data segments into an entirety by an integrated evaluation model.

11. The wearable electronic device of claim 1 wherein the light detector senses multiple physiological signals and communicates with a processor to:
    segment the physiological signals into several data segments;
    randomly split the segmented data into multiple data sets;
    extract features of the data segments in each data set;
    develop a segment evaluation model based on the multiple data sets with the extracted features of the data segments thereof; and
    develop an integrated evaluation model to integrate the evaluation results of the segment evaluation model into an entirety.

12. The wearable electronic device of claim 11, wherein the segmented data is randomly split into a training data set, a validation data set, and a testing data set, and the processor is configured to develop the segment evaluation model by:
    training a neural network with the extracted features of the data segments from the training and validation sets to develop the segment evaluation model; and
    testing the developed segment evaluation model based on the extracted features of the data segment from the testing set.

13. The wearable electronic device of claim 11, wherein the sensed physiological signals comprise a first group of signals for evaluating a sleep condition and a second group of signals indicating the sleep condition as a reference.

14. The wearable electronic device of claim 13, wherein the sleep condition comprises occurrences of severities of sleep disorder and sleep status during a target sleep period.

15. A wearable device, comprising:
a main body configured to be at least partially worn on an index finger of a hand of a user;
a functional component comprising an optical sensor coupled to or embedded in the main body for detecting physiological information of the user from a blood vessel of the index finger and configured to be place toward the thumb of the hand when worn; and
a matching unit coupled to the main body and operable for assisting the user to properly position the wearable device on the index finger and to reduce the rotation of the wearable device, the matching unit comprising an extending unit extending from the main body in an opposing direction to the functional component, and
the extending unit is configured to be coupled with an adjacent finger to align the device and place the functional component toward the thumb of the hand when worn.

16. The wearable device of claim 15, wherein the optical sensor comprises
a first light emitter to emit a first light;
a second light emitter to emit a second light; and
a light detector to detect reflected first and second light from the index finger.

17. The wearable device of claim 16, wherein the first and second light emitters and the light detector are arranged along a longitudinal direction of the index finger.

18. The wearable device of claim 15, wherein the sensor is detachable from the main body.

19. The wearable device of claim 15, wherein the matching unit comprises two extending units to hold a second digit adjacent to the index finger.

20. The wearable electronic device of claim 19, wherein the functional component is detachable from the main body, and the optical sensor is coupled with or integrated in the functional component.

* * * * *